United States Patent
Shih et al.

(10) Patent No.: US 10,961,564 B2
(45) Date of Patent: Mar. 30, 2021

(54) NANOPOROUS GOLD AND SILVER NANOPARTICLES AND SUBSTRATES FOR MOLECULAR AND BIOMOLECULAR SENSING

(71) Applicant: UNIVERSITY OF HOUSTON SYSTEM, Houston, TX (US)

(72) Inventors: Wei-Chuan Shih, Houston, TX (US); Richard Willson, Houston, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 0 days.

(21) Appl. No.: 15/314,219

(22) PCT Filed: May 22, 2015

(86) PCT No.: PCT/US2015/032314
§ 371 (c)(1),
(2) Date: Nov. 28, 2016

(87) PCT Pub. No.: WO2015/183758
PCT Pub. Date: Dec. 3, 2015

(65) Prior Publication Data
US 2017/0152549 A1 Jun. 1, 2017

Related U.S. Application Data

(60) Provisional application No. 62/004,131, filed on May 28, 2014.

(51) Int. Cl.
*C12Q 1/6816* (2018.01)
*G01N 21/65* (2006.01)
(Continued)

(52) U.S. Cl.
CPC ......... *C12Q 1/6816* (2013.01); *G01N 21/554* (2013.01); *G01N 21/648* (2013.01);
(Continued)

(58) Field of Classification Search
CPC .. C12Q 1/6816; G01N 21/648; G01N 21/554; G01N 33/54373; G01N 33/553; G01N 21/658; C12M 47/04
See application file for complete search history.

(56) References Cited

U.S. PATENT DOCUMENTS

2004/0086897 A1 5/2004 Mirkin et al.
2006/0246460 A1* 11/2006 Graham .................... G01J 3/44
                                                          435/6.11
2014/0104606 A1 4/2014 Shih

FOREIGN PATENT DOCUMENTS

WO  WO-2012039764 A1 * 3/2012 ............. B82Y 30/00

OTHER PUBLICATIONS

Hu et al. Talanta. 2010. 80:1737-1743. (Year: 2010).*
(Continued)

*Primary Examiner* — Joseph G. Dauner
(74) *Attorney, Agent, or Firm* — Jackson Walker LLP

(57) ABSTRACT

A methodology for assays and diagnostics utilizes a nanoporous or corrugated metal-containing surface, fiber or particle which enhances or suppresses the optical detectability of a label. The resulting optical, electromagnetic, or imaging signal signals the presence of a pathogen or analyte of interest. Preferred embodiments pertain to label-free, in situ monitoring of individual DNA hybridization in microfluidics using molecular sentinel probes immobilized on nanoporous gold disks. By immobilizing molecular sentinel probes on nanoporous gold disks, single-molecule sensitivity is demonstrated via surface-enhanced Raman scattering which provides robust signals. The described methodology is generally applicable to most amplification independent assays and molecular diagnostics.

10 Claims, 25 Drawing Sheets
Specification includes a Sequence Listing.

(51) Int. Cl.
  *G01N 21/64* (2006.01)
  *G01N 21/552* (2014.01)
  *G01N 33/543* (2006.01)
  *G01N 33/553* (2006.01)
(52) U.S. Cl.
  CPC ..... *G01N 21/658* (2013.01); *G01N 33/54373* (2013.01); *G01N 33/553* (2013.01)

(56) References Cited

OTHER PUBLICATIONS

Qiu et al. Colloids and Surfaces B: Biointerfaces. 2010 79:304-308. (Year: 2010).*
Wang et al. Analytica Chimica Acta. 2013. 786:153-158. (Year: 2013).*
Qi et al. Nanoscale. 2013. 5:4105-4109. (Year: 2013).*
Seker et al. Materials. 2009. 2:2188-2215. (Year: 2009).*
Wang et al. J Mater Chem. 2012. 22:5344-5348 (Year: 2012).*

The International Search Report and Written Opinion issued by the Korean Intellectual Property Office for PCT Application No. PCT/US2015/032314 dated Jul. 28, 2015.
The International Preliminary Report on Patentability issued by the International Bureau of WIPO for PCT Application No. PCT/US2015/032314 dated Nov. 29, 2016.
Ngo et al., "Multiplex detection of disease biomarkers using SERS molecular sentinel-on-chip", Analytical and Bioanalytical Chemistry, Epub., Feb. 28, 2014, pp. 3335-3344, vol. 406, issue 14.
Vo-Dinh et al., "Plasmonic nanoprobes for SERS biosensing and bioimaging", Journal of Biophotonics, 2010, pp. 89-102, vol. 3, No. 1-2.
Li et al., "Stamping surface-enhanced Raman spectroscopy for label-free, multiplexed, molecular sensing and imaging", Journal for Biomedical Optics, May 7, 2014, pp. 050501-1-05051-3, vol. 19, issue 5, article 050501.
Santos, et al., "Label-free, zeptomole cancer biomarker detection by surface-enhanced fluorescence on nanoporous gold disk plasmonic nanoparticles", Journal of Biophotonics, Feb. 24, 2015, pp. 1-9.
Zhao, et al., "Monolithic NPG nanoparticles with large surface area, tunable plasmonics, and high-density internal hot-spots", Nanoscale, (2014), 6, pp. 8199-8207.

* cited by examiner (a)

(b)

(a)

(b)

(a)

(b)

(a)

(b)

NANOPOROUS GOLD AND SILVER NANOPARTICLES AND SUBSTRATES FOR MOLECULAR AND BIOMOLECULAR SENSING

CROSS-REFERENCES TO RELATED APPLICATIONS

This application claims priority to U.S. Provisional Patent Application Ser. No. 62/004,131, filed May 28, 2014, entitled "Nanoporous Gold and Silver Nanoparticles and Substrates for Biomolecular Sensing," the entire contents of which is hereby incorporated by reference.

BACKGROUND

This disclosure pertains to molecular and biomolecular sensing, and particularly to a methodology for assays and diagnostics in which a nanoporous or corrugated metal-containing surface, fiber or particle, enhances or suppresses the optical detectability of a label or the target molecule of interest itself.

The detection of hydrocarbons, environmental contaminants, food components, biological molecules and cells, especially pathogens, DNA, mRNA and miRNA, viral RNA, proteins, and modified (e.g., phosphorylated) proteins, as well as biological processes, plays a central role in health, safety and research. There is an ongoing need for increased sensitivity of detection at reasonable cost. The needs of society for such assays are not fully met by any currently available method, and there is continuing development in this area.

As one example, DNA hybridization, where two single-stranded DNA (ssDNA) molecules form duplex through non-covalent, sequence-specific interactions, is a fundamental process in biology. Developing a better understanding of the kinetics and dynamic aspects of hybridization will help reveal molecular mechanisms involved in numerous biomolecular processes. To this end, sequence-specific detection of hybridization at the single-molecule level has been instrumental and gradually become a ubiquitous tool in a wide variety of biological and biomedical applications such as clinical diagnostics, biosensors, and drug development. Label-free and amplification-free schemes are of particular interest because they could potentially provide in situ monitoring of individual hybridization events, which may lead to techniques for discriminating subtle variations due to single-base modification without stringency control or repetitive thermal cycling. To further increase experimental robustness and productivity and reduce complexity, single-step assays are highly desirable.

For example, "sandwich" assay that involves multiple hybridization steps could generate highly convoluted results. Currently, intermolecular diffusion of DNA molecules is commonly studied by fluorescence correlation spectroscopy (FCS) with an observation time limited to the diffusion time of molecules through the observation volume. Single-molecule fluorescence resonance energy transfer (smFRET) and other fluorescence techniques have also been employed to study conformational changes. Unlike most fluorescence techniques, molecular beacons (MB) provide label-free detection of hybridization. However like most other fluorescence techniques, MB also suffers from rapid photobleaching which prevents prolonged observation for slow processes.

Of particular interest is the use of plasmonic materials for the sensing and detection of biomolecular components and processes. Metal nanostructures exhibit interesting optical properties due to their nanoscale features and the collective oscillation of conduction band electrons excited by incident light. The associated enhanced electric field near the surface of metal nanostructures, known as surface plasmon resonance (SPR) for propagating fields or localized surface plasmon resonance (LSPR) for non-propagating ones, has been well studied and is widely used in optical sensors, photovoltaic devices, waveguides, imaging devices, SHINERS and biomedicine. Both SPR and LSPR strongly depend on the composition, shape and size of metal nanostructures, as well as the ambient environment. Therefore, controlling their composition, shape and size is essential for potential applications.

In addition to fluorescence techniques, label-free techniques for hybridization detection and biosensing include the use of localized surface plasmon resonance (LSPR), extraordinary optical transmission, electrochemistry, circular dichroism spectroscopy and mass measurements, but these techniques can hardly provide the sensitivity for single-molecule detection.

Recently, molecular beacon (MB) probes have been immobilized on plasmonic nanoparticles to harness metal-enhanced fluorescence and achieved a limit of detection (LOD) ~500 pM. Carbon nanotube field-effect transistor has been demonstrated to provide label-free, single-molecule detection at relatively high target concentrations (100 nM to 1 µM). Greater sensitivity is still needed.

SUMMARY

The present disclosure relates generally to the use of nanostructured materials such as nanoporous gold and silver in biomolecular sensing applications. In particular, the present disclosure relates to monitoring of biological processes using probes immobilized on nanoporous gold or silver nanoparticles. Preferred embodiments pertain to label-free, in situ monitoring of individual DNA hybridization in microfluidics using molecular sentinel probes immobilized on nanoporous gold disks. By immobilizing molecular sentinel probes on nanoporous gold disks, single-molecule sensitivity is demonstrated via surface-enhanced Raman scattering which provides robust signals without photobleaching for more than an hour. Target concentrations as low as 20 pM can be detected within 10 min by diffusion-limited transport.

Nanoporous gold (NPG) as a bulk nanostructured material is produced by dealloying the less noble constituent of a gold alloy in concentrated nitric acid or via electrochemistry. The nanoporous structure has a bicontinuous and open porosity and demonstrates tunable ligament and nanopore sizes ranging from a few nanometers to several microns. Its high specific surface area, crystalline alignment and clean surface make NPG an attractive active catalyst material requiring no support. Besides its catalytic activity, NPG also shows interesting optical properties such as mixed localized/propagating surface plasmons because of the nanoscale ligaments and pore channels within the unique 3D bicontinuous porous nanostructures. The plasmonic properties of NPG have been explored for molecular sensing using "as-dealloyed", mechanically stamped, or wrinkled films as well as lithographically patterned monolithic NPG disks with a diameter smaller than the wavelength of natural light. The enhanced electromagnetic fields of LSPR excited in the ligaments are considered to be a major contributor to surface-enhanced optical phenomena such as surface-enhanced Raman scattering (SERS), surface-enhanced fluorescence, etc.

In "as-dealloyed" NPG films, the LSPR band centered around 600 nm has a limited tunability of about 50 nm, achieved by varying the pore size from 10 to 50 nm. In mechanically-stamped NPG films, the grating modulation provides a propagating SPR mode coupled with NPG's original LSPR band. However, the grating modulation does not (red)-shift the original NPG LSPR band. In thermally-wrinkled NPG, random plasmonic hot spots form at gaps and junctions due to structural deformation, but do not significantly alter the LSPR over the length scale of interest.

Methods of nanofabrication of uniform, monolithic disk-shaped NPG nanoparticles have been developed and their plasmonic properties have been investigated. Substrate-bound NPG disks can be released and harvested as colloidal nanoparticles, which differ drastically from existing NPG materials, and can be viewed as a novel functional material. NPG disks feature a well-defined "exterior" disk shape 100-1000 nm in diameter and 30-120 nm in thickness, and an "interior" 3-dimensional porous network with pore size ~5-20 nm. NPG disks exhibit nanoporosity mimicking that of mesoporous silica while, however, they are plasmonic. NPG disks' structural hierarchy differs from existing plasmonic nanoparticles such as Au or Ag nanospheres, nanorods, nanoshells, and nanocages. An NPG disk is an integral, monolithic construct, which differentiates it from nanoparticle aggregates. Therefore, NPG disks are a new form of nanomaterials which possess well defined exterior parameters, large specific surface areas, plasmonic properties and structural integrity and stability. NPG disks promote coupling between two LSPR, one original to the NPG, and the other from the external disk shape, providing highly tunable plasmonic properties with great utility in assays and diagnostics.

The present disclosure provides a methodology for assays and diagnostics in which nanoporous or corrugated metal-containing surface, fiber or particle, enhances or suppresses the optical detectability of a label. The resulting optical, electromagnetic, or imaging signal signals the presence of a pathogen or analyte of interest. The described methodology is generally applicable to most amplification independent assays and molecular diagnostics. The present disclosure also demonstrates enhanced sensitivity and convenience of use.

In principle, NPG can be patterned into any shape. Here disk-shaped NPG disks are used as an example. NPG disks with Raman or fluorescent brightness due to associated organic or inorganic reporter molecules and decorated with antibodies to a target over their whole surface are useful as detection reagents. The antibodies and/or fluors optionally can be destroyed on one side of the disks, e.g., using an ion beam. Antibodies can be replaced or supplemented with DNA probes, aptamers, cells, enzymes, PNA (peptide nucleic acid chimera), lectins, substrates, cells, carbohydrates, etc. Disks can be captured (or analyte-bridged) on a surface, e.g. in a microwell or microfluidic device, or captured in a flow-through or lateral-flow assay matrix. They may be dragged, floated, or settled in or out of an observation location by association with buoyant, dense, or electro- or magnetophoretically-mobile moiety, including a polymer, bubble, particle, or polyelectrolyte. Disks can be fabricated with fluorescent/Raman-active material on one side and antibodies on the other, or with magnetic elements included, or a number of other combinations, to achieve the desired effect.

As described in more detail below, nucleic acids whose plasmonic-enhanced optical properties can be modulated by analytes (e.g., sentinels, aptamers, etc.) can directly signal the presence of analytes by changes in Raman or fluorescence intensity. Analytes also can competitively suppress the binding of labeled analyte analogs (e.g., nucleic acids bearing dyes, fluors or Raman-active materials) to capture agents (e.g., PNA or DNA probes) on a plasmonic surface.

Raman or fluorescence detection of label molecules is most sensitive when the label is closely juxtaposed to the surface of the plasmonic material. Modification of the plasmonic surface with affinity agents such as antibodies, etc. impairs this proximity. Non-specific capture of labels directly on a plasmonic surface by adsorption, electrophoresis, or diffusion allows very high sensitivity, but requires that the presence of the labels in a location to be contacted with the plasmonic surface be strictly conditional upon the presence or absence of the analyte. This dependence can be achieved by competitive displacement of labels (or NPG disks or other materials) into a stream or volume which enters an observation point. It also can be achieved by size- or mobility-dependent removal of labels from the stream or volume, e.g. by non-specific adsorbent moieties shielded behind a size-selective moiety, as in the internal-surface reversed phase materials.

Surface-enhanced Raman scattering (SERS) is useful as a reporting mechanism for molecular sensing. SERS is an attractive approach for label-free multiplexed DNA/RNA detection because of its single-molecule sensitivity, molecular specificity, and freedom from quenching and photobleaching. These distinct advantages have led to the development of a number of SERS sensing platforms for single DNA hybridization detection, including the crescent moon structures, nanodumbbells, and Au particle-on-wire sensors. These SERS sensing platforms were able to achieve extremely high enhancement of local electromagnetic fields from "hot spots" by careful control of nanostructural assemblies.

A SERS-based label-free approach capable of in situ monitoring of the same immobilized ssDNA molecules and their individual hybridization events over more than an hour is presented here.

DETAILED DESCRIPTION OF PREFERRED EMBODIMENTS

Figure 1:
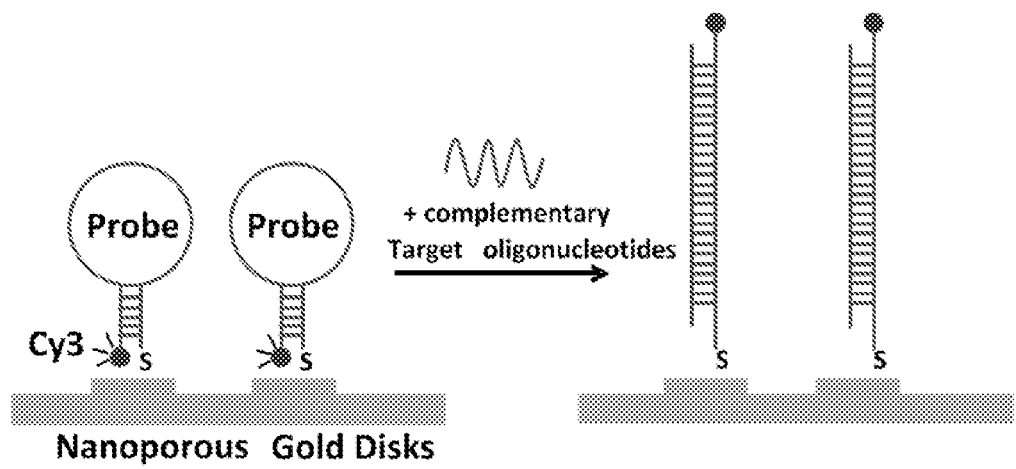
FIG. 1 shows (a) a schematic of the molecular sentinel reporting mechanism on NPG disk substrates and (b) SERS spectra of ERBB2 MS probes on MPG disk substrates.
Figure 1:
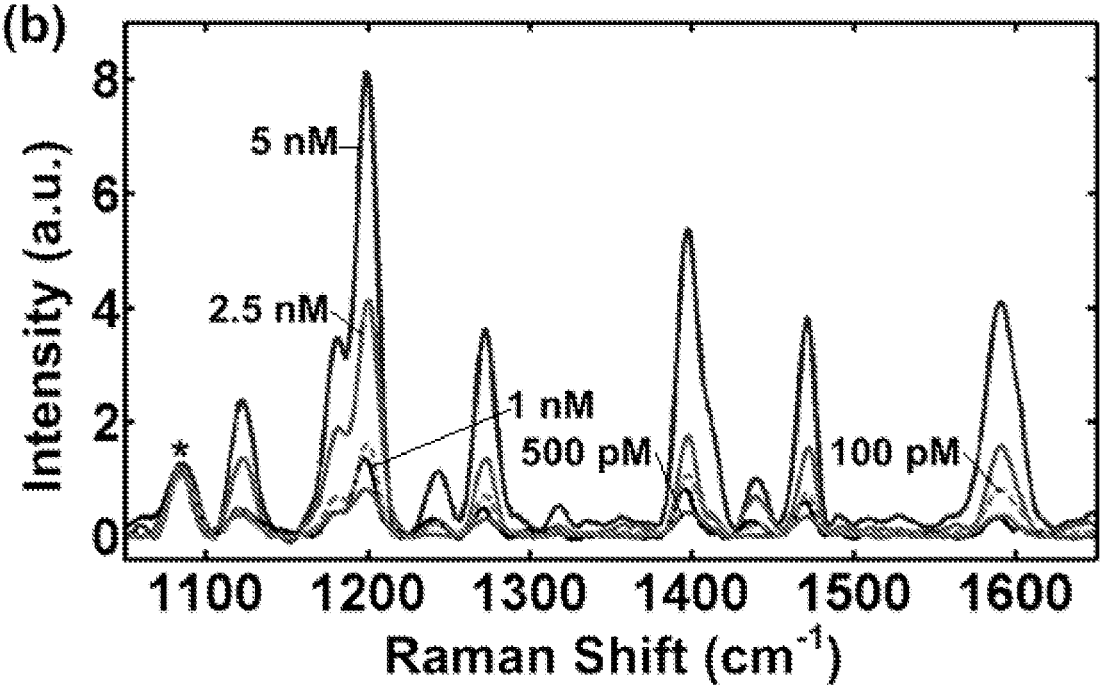

The present disclosure demonstrates the successful implementation of molecular sentinel (MS) technology immobilized on nanoporous gold (NPG) disks inside microfluidics. The microfluidic environment prevents sample drying, allows small sample volume, and permits agile fluid manipulation. MS involves the design of the complementary sequence of a target ssDNA into a stem-loop "hairpin". As shown in FIG. 1(a), the hairpin probe has a thiol group at the 5' end for robust immobilization on gold nanostructures, and a fluorophore such as cyanine 3 (Cy3) at the 3' end for SERS detection. Cy3 yields a strongly enhanced SERS signal when the probe is in the hairpin configuration. Intense SERS signals are observed due to the short distance between Cy3 molecules and the gold surface. Probes become straight and rigid after hybridization with target ssDNA molecules (right). This signal decreases when the probe is hybridized with the target and moves away from the surface. The SERS signal disappears because Cy3 molecules now are about 10 nm away from the gold surface. FIG. 1(b) shows the SERS spectra of the ERBB2 MS probes on NPG disk substrates by incubation (500 pM-5 nM) and drop cast (100 pM) immobilization protocols. The spectral baselines were approximated by a $5^{th}$ order polynomial and removed.

MS is label-free, requires only a single hybridization step, and can be multiplexed. MS has been employed to detect breast cancer marker genes ERBB2 and RSAD2 at concentrations of 1-500 nM using colloidal silver nanoparticles. Biomarker Ki-67 at ~1 µM has been demonstrated using a triangular-shaped nanowire substrate, resembling a "biochip" approach, which is particularly attractive for point-of-care applications where minimal sample preparation is desired.

The plasmonic substrate of choice here consists of a dense monolayer of NPG disks featuring a unique 3-dimensional internal porous network. The large surface area of NPG disks and hot-spots inside the nanoporous structures have contributed to an average SERS enhancement factor exceeding $10^8$ and surprisingly high photothermal conversion efficiency (>50%) among metal nanoparticles of similar size with various shapes and compositions. First, the patterned NPG disk substrates provide enough SERS enhancement to enable single-molecule observation of immobilized MS probes under stringent quantity control. Second, MS on NPG disks can be employed to perform time-lapse in situ monitoring of hybridization. Finally, individual DNA hybridization events can be observed and quantified as early as ~10 min after introducing 20 pM complementary target ssDNA molecules.

The present disclosure relates to a label-free technique to detect trace molecules such as hydrocarbons, thiols, various dye molecules, and in situ monitor DNA hybridization using molecular sentinel probes immobilized on patterned nanoporous gold disk SERS substrates. Taking advantage of the ultrahigh SERS sensitivity of these novel substrates, which enables detection of individual Cy3-labeled DNA probe molecules, single DNA hybridization events were observed by in situ monitoring the hybridization process. In addition, the onset of hybridization events was detected within ~10 min after introducing 20 pM target ssDNA molecules. Given the single-molecule sensitivity, robust SERS signals, and simple detection system, this approach could find potential applications in time-lapsed monitoring of DNA interactions and point-of-care applications.

In addition to SERS, the present disclosure also relates to surface-enhanced fluorescence (SEF), also known as metal enhanced fluorescence (MEF), to monitor various fluorescent molecules such as biological labels and polycyclic aromatic hydrocarbon (PAH) which are common environmental toxins. Further, the present disclosure relates to using LSPR to detect local refractive index variations due to surface adsorption and/or binding of molecular analytes. Moreover, the present disclosure relates to using surface-enhanced near infrared (SENIR) detection to measure vibrational overtones and combination bands in the wavelength range of 1000-2400 nm. The types of detectable analytes include neurotransmitters such as dopamine and serotonin; urinary analytes such as creatinine, urea, and various proteins; and other physiological analytes such as glucose.

In the present method for in situ monitoring of biomolecular processes, the plasmonic material can be NPG, patterned NPG, NPG disk, nanoporous noble metal, patterned nanoporous metal alloy, NPG particle, composite structure with nanoporous and magnetic material, or nanoporous ribbon. The plasmonic particle number can be one to one trillion. The preferred particle density can be one to one billion per microliter. The particle loading with recognition element can be one per particle to one trillion per particle. The particle can be disk shaped, lozenge shaped, square shaped, or oval shaped.

The relocation/separation aid for analyte-dependent relocation of Raman or fluor-active reporter can be polyelectrolyte, aqueous two-phase system, nanoparticle, gold particle, silver particle, polymer, drag tag, magnetic particle, buoyant particle, microbubble, metal particle, charged moiety, dielectrophoresis tag, smart polymer, or NIPAAM.

The target analyte can be Cell surface receptor, protein, nucleic acid, mRNA, genomic DNA, PCR product, cDNA, peptide, hormone, drug, spore, virus, SSU RNAs, LSU-rRNAs, 5S rRNA, spacer region DNA from rRNA gene clusters, 5.8S rRNA, 4.5S rRNA, 10S RNA, RNAseP RNA, guide RNA, telomerase RNA, snRNAs—e.g. U1 RNA, scRNAs, Mitochondrial DNA, Virus DNA, virus RNA, PCR product, human DNA, human cDNA, artificial RNA, siRNA, enzyme substrate, enzyme, enzyme reaction product, Bacterium, virus, plant, animal, fungus, yeast, mold, Archae; Eukaryotes; Spores; Fish; Human; Gram-Negative bacterium, $Y.$ pestis, HIV1, B. anthracis, Smallpox virus, Chromosomal DNA; rRNA; rDNA; cDNA; mt DNA; cpDNA, artificial RNA, plasmid DNA, oligonucleotides; PCR product; Viral RNA; Viral DNA; restriction fragment; YAC, BAC, cosmid, hormone, drug, pesticide, digoxin, insulin, HCG, atrazine, anthrax spore, teichoic acid, prion, chemical, toxin, chemical warfare agent, pollutant, Genomic DNA, methylated DNA, messenger RNA, fragmented DNA, fragmented RNA, fragmented mRNA, mitochondrial DNA, viral RNA, microRNA, in situ PCR product, polyA mRNA, RNA/DNA hybrid, protein, glycoprotein, lipoprotein, phosphoprotein, specific phosphorylated variant of protein, virus, chromosome, enzyme, agricultural chemical, toxin, preservative, species-variant of a protein, pesticide, or herbicide.

Samples containing the target analyte can be blood sample, air filtrate, tissue biopsy, fine needle aspirate, cancer cell, surgical site, soil sample, water sample, whole organism, spore, genetically-modified reporter cells, Body Fluids (blood, urine, saliva, sputum, sperm, biopsy sample, forensic samples, tumor cell, vascular plaques, transplant tissues, skin, urine; feces, cerebrospinal fluid); Agricultural Products (grains, seeds, plants, meat, livestock, vegetables, rumen contents, milk, etc.); soil, air particulates; PCR products; purified nucleic acids, amplified nucleic acids, natural waters, contaminated liquids; surface scrapings or swabbings; Animal RNA, cell cultures, pharmaceutical production cultures, CHO cell cultures, bacterial cultures, virus-infected cultures, microbial colonies, FACS-sorted population, laser-capture microdissection fraction, magnetic separation subpopulation, or FFPE extract.

Sample preparation agents can be acid, base, detergent, phenol, ethanol, isopropanol, chaotrope, enzyme, protease, nuclease, polymerase, adsorbent, ligase, primer, nucleotide, restriction endonuclease, detergent, ion exchanger, filter, ultrafilter, depth filter, multiwell filter, centrifuge tube, multiwell plate, immobilized-metal affinity adsorbent, hydroxyapatite, silica, zirconia, magnetic beads, Fine needle, microchannel, deterministic array, size-selective adsorbent, aqueous two-phase system.

Sample preparation methods can be Filter, Centrifuge, Extract, Adsorb, protease, nuclease, partition, wash, de-wax, leach, lyse, amplify, denature/renature, electrophoresis, precipitate, germinate, Culture, PCR, disintegrate tissue, extract from FFPE, LAMP, NASBA, emulsion PCR, phenol extraction, silica adsorption, IMAC, filtration, affinity capture, microfluidic processing, or selective adsorption.

The location of the monitoring can be well plate, filter, immunochromatographic assay, immunoassay, hybridization assay, biopsy specimen, in situ, in patient, in surgical incision, surface, cell surface, thin section, self-assembled array, in solution, in suspension, or on a microfluidic chip.

The recognition element for the detection or monitoring can be antibody, nucleic acid, carbohydrate, aptamer, ligand, chelators, peptide nucleic acid, locked nucleic acid, backbone-modified nucleic acid, lectin, padlock probe, substrate, receptor, viral protein, mixed, cDNA, metal chelate, boronate, peptide, enzyme substrate, enzyme reaction product, lipid bilayer, cell, tissue, insect, microorganism, yeast, bacterium, anti-RNA/DNA hybrid antibody, mutS, anti-DNA antibody, anti-methylation antibody, or anti-phosphorylation antibody.

The immobilization chemistry can be Avidin/biotin, amine, carbodiimide, thiol, gold/thiol, metal chelate affinity, aldehyde, mixed-ligand, adsorptive, covalent, SAM, DSP, EDC, or Trauton's reagent. Illumination can be by laser, xenon lamp, LED, arc lamp, mercury lamp, incandescent, fluorescent, scanned, time-modulated, frequency-modulated, chopped, time-gated, polarized, infrared, visible, UV, CDMA encoded, multiangle, or ring. Detection can be by eye, camera, digital camera, PMT, scanner, microscope, telescope, detector array, time-gated, chopped, frequency-modulated, wavelength-filtered, polarization-sensitive, Raman, Surface-enhanced Raman, high numerical aperture, color-sensitive, lifetime, FRET, FRAP, intensified, phosphorescence, resistivity, ellipsometer, high-density CCD, in flow, on surface, or in suspension.

The surface coating for the detection particle can be antibody, nucleic acids, PEG, dextran, protein, polymer, lipid, metal, or glass. The particle can be 1 nm-3 mm in size. The detection volume can be 1 fL to 3 mL.

The present method could be useful for Clinical Diagnosis; Prognosis, Pathogen discovery; Biodefense; Research; Adulterant Detection; Counterfeit Detection; Food Safety; Taxonomic Classification; Microbial ecology; Environmental Monitoring; Agronomy; or Law Enforcement.

Nanoporous Gold Disks

Plasmonic metal nanostructures have shown great potential in sensing, photovoltaics, imaging and biomedicine, principally due to enhancement of the local electric field by light-excited surface plasmons, the collective oscillation of conduction band electrons. Thin films of nanoporous gold have received a great deal of interest due to the unique 3-dimensional bicontinuous nanostructures with high specific surface area. However, in the form of semi-infinite thin films, nanoporous gold exhibits weak plasmonic extinction and little tunability in the plasmon resonance, because the pore size is much smaller than the wavelength of light. By making nanoporous gold in the form of disks of sub-wavelength diameter and sub-100 nm thickness, these limitations can be overcome. Nanoporous gold disks not only possess large specific surface area but also high-density, internal plasmonic "hot-spots" with impressive electric field enhancement, which greatly promotes plasmon-matter interaction as evidenced by spectral shifts in the surface plasmon resonance. In addition, the plasmonic resonance of nanoporous gold disks can be easily tuned from 900 to 1850 nm by changing the disk diameter from 300 to 700 nm. Furthermore, nanoporous gold disks can be fabricated as either bound on a surface or as non-aggregating colloidal suspension with high stability.

Substrate-bound NPG disks can be released and harvested as colloidal nanoparticles, which differ drastically from existing NPG materials, and can be viewed as a novel functional material. NPG disks feature a well-defined "exterior" disk shape 300-700 nm in diameter and 75 nm in thickness, and an "interior" 3-dimensional porous network with pore sizes ~13 nm. NPG disks inherit LSPR features from both the nanoporous structures and the sub-wavelength disk shape. The coupling between these two LSPR results in intriguing plasmonic properties. Nanoporous plasmonic disks not only possess large specific surface area but also high-density internal plasmonic "hot-spots" with impressive electric field enhancement, which greatly promotes plasmon-matter interactions as evidenced by the high LSPR sensitivity to the ambient environment.

Figure 2:
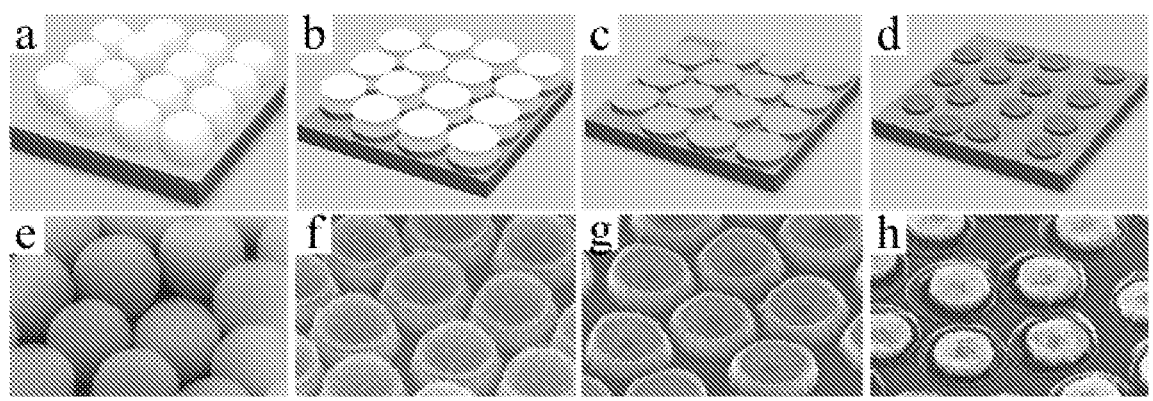
FIG. 2 shows the fabrication process used to prepare NPG disks, (a) formation of a monolayer of polystyrene (PS) beads, (b) $O_2$ plasma shrinkage of the PS beads and AR sputter etching, (c) selective dissolver of PS beads by chloroform, (d) formation of NPG disks by dealloying, and (e)-(h) SEM images taken at each step of the process.

FIG. 2 (a)-(d) illustrate the fabrication process used to prepare NPG disks on a silicon (or glass) substrate: (a) formation of a monolayer of polystyrene (PS) beads on an alloy-coated silicon (or glass) substrate; (b) $O_2$ plasma shrinkage of the PS beads and Ar sputter etching to form isolated alloy disks; (c) selective dissolver of PS beads by chloroform; (d) formation of NPG disks by dealloying. FIG. 2 (e)-(h) shows SEM images taken at each step of the process with a 45° viewing angle. Additional experimental data and discussion is found in Example 1 below.

Generally, to fabricate NPG disks, both top-down lithographic patterning and bottom-up atomic dealloying are taken advantage of, which together demonstrate great synergy in precisely tuning the plasmonic properties of nanoporous materials. As shown in FIG. 2, a film of gold and silver alloy approximately 120 nm thick was first sputter deposited onto a substrate (e.g., silicon wafer or glass slide) using an $Ag_{82.5}Au_{17.5}$ (atomic percentage) alloy target. A monolayer of 460-1100 nm size polystyrene beads (PS) was then formed on top of the alloy film. Over 90% of the alloy surface covered with close-packed PS beads can typically be achieved reproducibly (FIG. 2(a)). Next, a timed oxygen plasma treatment was employed to shrink the PS beads, thus separating them from neighboring beads. The sample was then sputter-etched in Argon plasma to transfer the bead pattern into the alloy film (FIG. 2(b)). Once the pattern transfer was completed, the PS beads were removed (FIG. 2(c)). The alloy disks were dealloyed in concentrated nitric acid, followed by rinsing in deionized (DI) water (FIG. 2(d)) to produce the array format NPG disks. There was substantial size shrinkage during the PS bead etching step as well as the dealloying process. Scanning electron microscopy (SEM) images (FIG. 2((e)-(h)) show the corresponding nanostructures through the fabrication steps. To produce suspended colloidal NPG disks, high-density NPG disk arrays on a 3-inch Si wafer were further sonicated in DI water.

Figure 3:
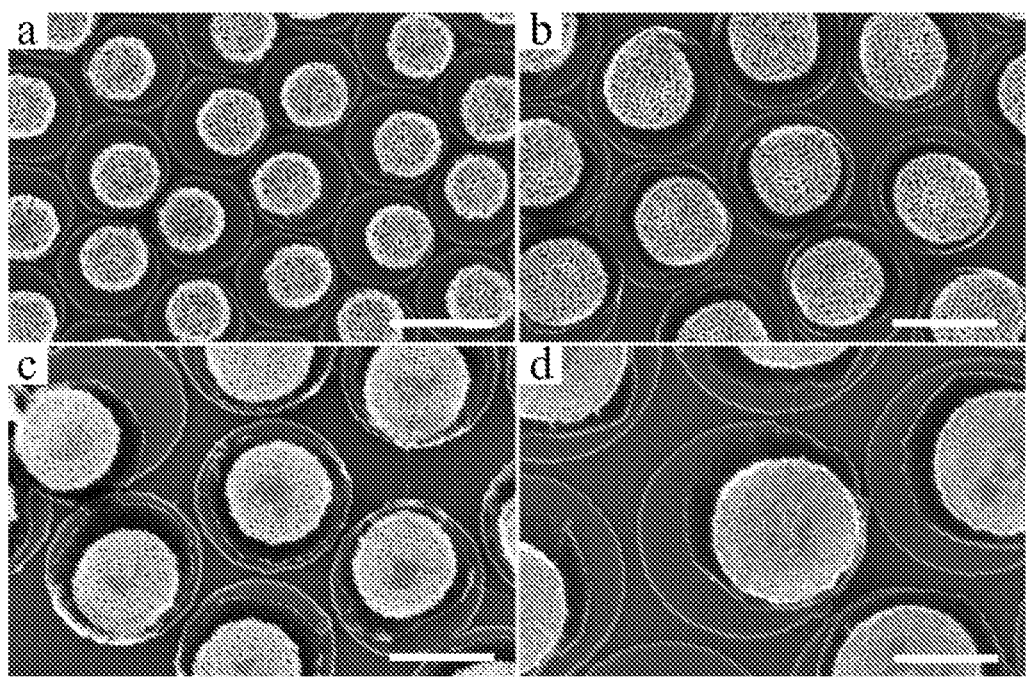
FIG. 3 shows SEM images of NPG disks made using 460±9, 600±12, 800±9 and 1100±14 nm PS beads on Si substrates with corresponding diameters of (a) 300±7, (b) 400±10, (c) 500±6 and (d) 700±13 nm, respectively.

FIG. 3 shows SEM images of monolayer samples of NPG disks on Si substrates. The mean size and the standard deviation of different NPG disks are determined by measuring ~100 disks in SEM images for each set of samples. The NPG disks obtained by using PS beads with original sizes 460±9, 600±12, 800±9 and 1100±14 nm were 300±7, 400±10, 500±6 and 700±13 nm in diameter, respectively. The scale bar is 500 nm. The small size dispersion confirms the high fidelity of the pattern-transfer process. Compared to the original sizes of the PS beads, there is an approximate 33-37% decrease in NPG disk diameter, of which ~5% occurs during the oxygen plasma treatment and up to 32% occurs during the dealloying process. The thickness also shrank from 120 to 75 nm. These values are consistent with ~30% volume reduction by electrochemical dealloying of Au—Ag alloys because of plastic deformation. Simulations of geometric relaxation in bicontinuous nanoporous metals revealed that surface relaxation played a significant role in the dramatic shrinkage during selective dissolution. Recently, similar size shrinkage ~29% was reported by Dong and coworkers after dealloying Au—Ag alloy ($Ag_{77}Au_{23}$, at %) in nitric acid.

NPG disks can move off-site during dealloying, as indicated by the presence of off-centered NPG disks with respect to the silicon etch marks during the Ar sputter-etching step. The adhesion between Si and sputtered Au—Ag alloy was weakened due to the oxidation of silicon to $SiO_2$ by concentrated nitric acid. Therefore, the strong stress generated by volume shrinkage plausibly led to movement of the NPG disks. NPG disks were easily released from the Si substrate by sonication due to the weak adhesion, which was nevertheless sufficiently strong to hold the disks in place while rinsing with water. Furthermore, the "unconstrained" shrinkage led to NPG without cracks, in contrast to NPG disks that were strongly immobilized on Au substrates in our previous study. Crack-free NPG disks are essential for preserving the monolithic structural integrity during and after the release process, as well as the uniformity of the nanoporous network. The corresponding pore sizes for the 300-700 nm diameter NPG disks were 13.8±2.2, 13.7±2.9, 12.5±2.0 and 12.8±2.4 nm, respectively (Table 1 below). The total surface area was about seven-fold the projected geometrical area with pore size ~13 nm by SEM image analysis based on ImageJ software (See Table 1).

Table 1 shows the average diameter, pore size, roughness factor, and zeta potentials (ζ) of the as-prepared NPG disks. The thickness of the NPG disks was 75±1 nm.

TABLE 1

| NPG disk samples[a] | Average diameter (nm) | Average pore size (nm) | Roughness factor[b] | ζ (mV)[c] | FWHM of the in-plane peak[d] (nm) |
|---|---|---|---|---|---|
| 1 | 300 ± 7 | 13.8 ± 2.2 | 6.56 ± 0.38 | −28.5 ± 2.1 | 421.9 |
| 2 | 400 ± 10 | 13.7 ± 2.9 | 7.38 ± 0.41 | −26.4 ± 3.2 | 460.9 |
| 3 | 500 ± 6 | 12.5 ± 2.0 | 7.71 ± 0.11 | −19.0 ± 1.3 | 717.6 |
| 4 | 700 ± 13 | 12.8 ± 2.4 | 7.65 ± 0.27 | −22.7 ± 1.2 | 1329.8 |

[a]NPG disks were made by using 460, 600, 800 and 1100 nm PS beads as masks and identical alloy thickness.
[b]The roughness factor was obtained by using expression 3 hβ/r, where h, β, and r are the NPG disk thickness, 2-dimensional porosity, and mean pore radius, respectively. The analysis was based on ImageJ software (NIH).
[c]Zeta potentials were measured in DI water.
[d]The full width at half maximum (FWHM) of the in-plane peaks of NPG disks obtained in air (n = 1) was measured by the GRAMS/AI.

Figure 4:
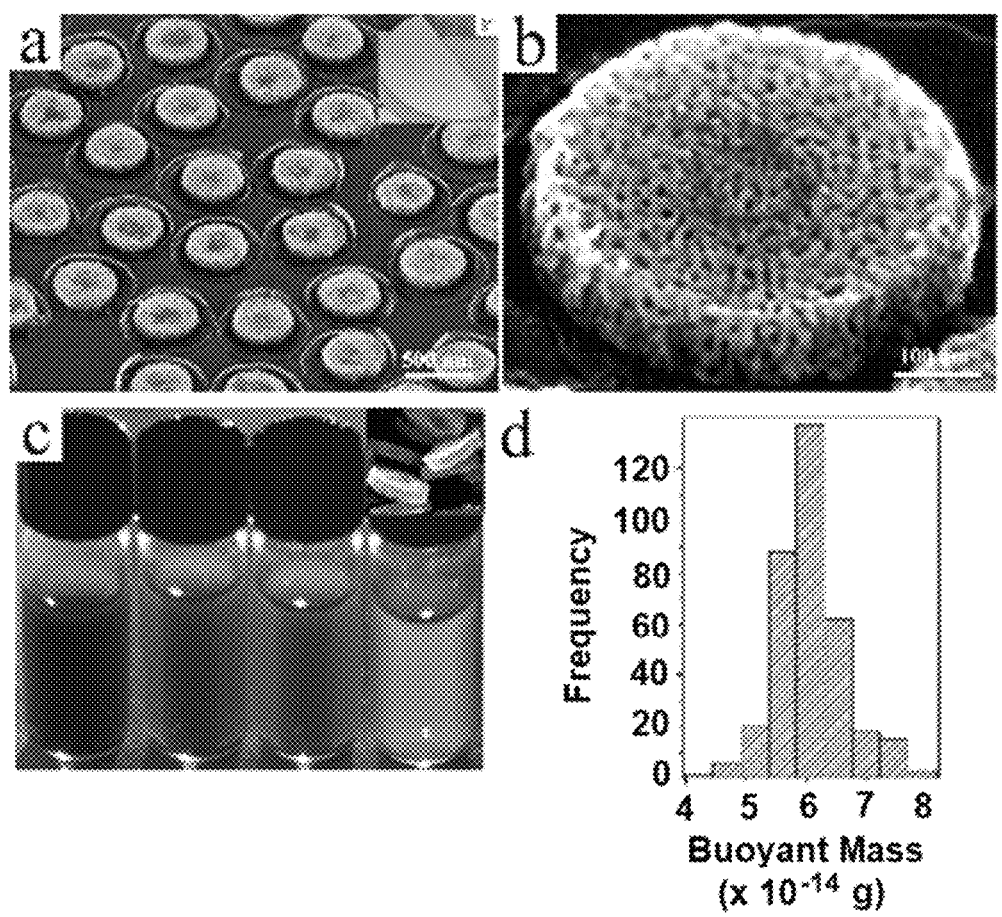
FIG. 4 shows (a) SEM image of high density NPG disk arrays on Si wafer before release, with inset showing 3" silicon wafer covered by a high-density monolayer of PS beads, (b) SEM image of a single NPG disk with a diameter of 500 nm, (c) NPG disks having different sizes 300±7, 400±10, 500±6, and 700±13 nm (from left to right) after release from the substrates to form colloidal NPG disk suspensions, with an inset of the SEM image of NPG disks released from the substrate by sonication, dropped and dried on a Si wafer, and (d) histogram of 400 nm NPG disk buoyant mass distribution measured by flowing colloidal NPG disks in the microfluidic channel.

FIG. 4 shows SEM images of NPG disks taken at a 45° viewing angle, stored in DI water, and single disk buoyant mass measurements. FIG. 4(a) shows high density NPG disk arrays on Si wafer before release. The inset is a 3" silicon wafer covered by a high-density monolayer of PS beads. FIG. 4(b) shows a single NPG disk with a diameter of 500 nm. FIG. 4(c) shows NPG disks having different sizes 300±7, 400±10, 500±6, and 700±13 nm (from left to right) after released from the substrates by sonication in DI water to form colloidal NPG disk suspensions. The inset is the SEM image of NPG disks released from the substrate by sonication, dropped and dried on a Si wafer. FIG. 4(d) shows a histogram of 400 nm NPG disk buoyant mass distribution measured by flowing colloidal NPG disks in the microfluidic channel, with an average of 6.04×10$^{-14}$±7.6×10$^{-15}$ g.

FIG. 4 displays three different views of NPG disks to further show the capability of preparing the both arrayed and colloidal NPG disks. FIGS. 4a and b show high-density NPG disk arrays on a 3-inch Si wafer and SEM image of a single NPG disk, respectively. With the aid of sonication, NPG disks were released from the substrates into DI water to form colloidal NPG disk suspensions (FIG. 4c). The inset shows colloidal NPG disks dried on a Si wafer. Surfactant-free NPG disks were easily transferred to DI water without aggregation. Therefore, by flowing individual colloidal NPG disks in microfluidic channels, single disk (400 nm diameter) buoyant mass was determined to be 6.04×10$^{-14}$±7.6×10$^{-15}$ g as shown in FIG. 4d. For comparison, 400 nm diameter Au disks were fabricated without porous structures through nearly identical procedures. These Au disks immediately formed aggregates in millimeter size range in an aqueous solution upon release from the substrates. To understand the unique colloidal stability of the NPG disks, their zeta potentials were measured to elucidate their surface charge state (see Table 1 above). In general, when the absolute value of the zeta potential is larger than 25 mV, a nanoparticle suspension has a high degree of stability due to strong electrostatic repulsion between particles. The zeta potentials of the 300 and 400 nm NPG disks were −28.5±2.1 and −26.4±3.2 mV, respectively, suggesting that both sizes of colloidal NPG disks had negatively charged surfaces and were quite stable in solution, which was consistent with observations. Although the 500 and 700 nm diameter NPG disks possess negative surface charges but with slightly smaller zeta potentials, these larger NPG disks also exhibit practically-useful long-term stability (i.e., no/minimal aggregation when stored in DI water at 4° C. for 4 months).

Figure 17:
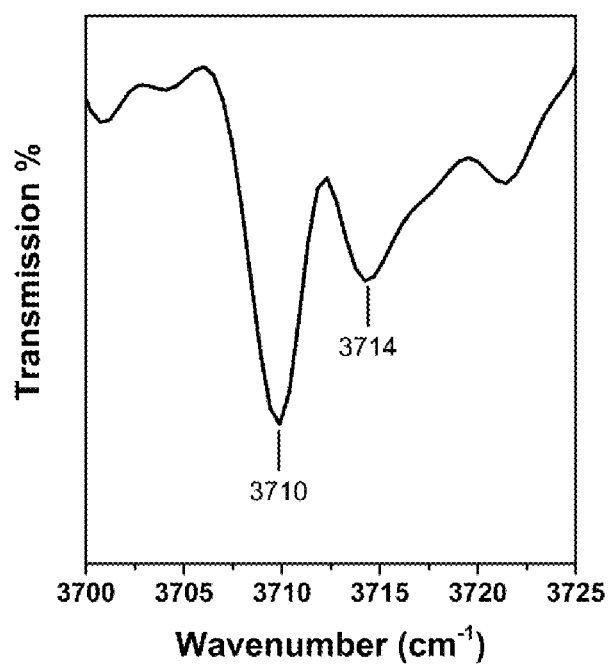
FIG. 17 shows the IR spectrum of 400 nm dried NPG disks.

The observed negative surface charge could be explained by the presence of deprotonated hydroxyl groups at the surface of NPG disks in aqueous solutions, which would plausibly form during the dealloying process in nitric acid. Hydroxyl groups formed on metal or metal oxide surfaces exhibit a stretching band at 3710 cm$^{-1}$ in infrared (IR) spectroscopic analysis. As shown in FIG. 17, the observed OH stretching band of dried 400 nm NPG disks at 3710 cm$^{-1}$ was consistent with the presence of hydroxyl groups on the surface of NPG disks. Inter-particle van der Waals forces are known to be affected by surface roughness and geometric factors, where surface roughness minimizes van der Waals interaction by limiting the contacts between the particles. In the case of NPG disks, where the surfaces are unquestionably rough, the aggregation could also be suppressed by reduced van der Waals forces. Therefore, NPG disks exhibit much greater stability than Au disks because of their negative surface charge and their unique nanoporous structures. Their superior stability and potential for facile surface modification/functionalization would offer a wide range of applications in a variety of fields ranging from biosensing and drug delivery to catalysis and plasmonics.

In the past few years, various NPG material parameters have been extensively studied, including grain size and boundaries by X-ray diffraction, crystal-facet orientations by high-resolution TEM (HRTEM), and atomic composition by X-ray photoelectron spectroscopy (XPS). NPG materials are known to contain residual silver content and other process-associated or environmental substances, and can be characterized by XPS, which is sensitive to the top ~10 nm of non-porous substrates. The XPS spectrum from 0 to 1200 eV of NPG disks drop-coated on a Si wafer, shows major peaks originated from Au and Ag and other elements such as Si, O, N and C. The Si wafer as well as the surface layer of SiO$_2$ on the wafer mainly contributed to Si and O. Trace amounts of nitrogen are observed, and a peak of N is at 400.2 eV can be assigned to N$^-$ in metal-N species formed during the sputtering etching. The XPS spectrum indicates that the porous structures of NPG disks generated by concentrated nitric acid had a clean surface except for minor surface contamination by carbon, which can plausibly come from the environment.

The chemical states of the NPG disks can also be identified by XPS. Ag 3d peaks of NPG disks show the binding energy of 3d$_{5/2}$ was 367.9 eV, slightly lower binding energy than that of metallic Ag (368.3 eV). The shift to lower binding energy is typical for oxidized Ag species. The oxidation of Ag likely occurred during the dealloying process. In addition, rehybridization effects in the Au—Ag alloy that reduce the electron density of silver, could also lead to lower Ag binding energies. For Au, both the peak shapes and the Au 4f binding energies (4f$_{5/2}$ 83.9 and 4f$_{7/2}$ 87.6 eV) were consistent with a metallic state. XPS surface compositional analysis revealed that ~24% residual Ag remains on the surface of the NPG disks. Segregation of Ag from the bulk to the surface region is known to occur in metal alloys. Consequently, NPG disks exhibit a clean surface with little contamination and negligible interference from residual silver, which can be important for sensing, SERS and catalysis applications.

Figure 5:
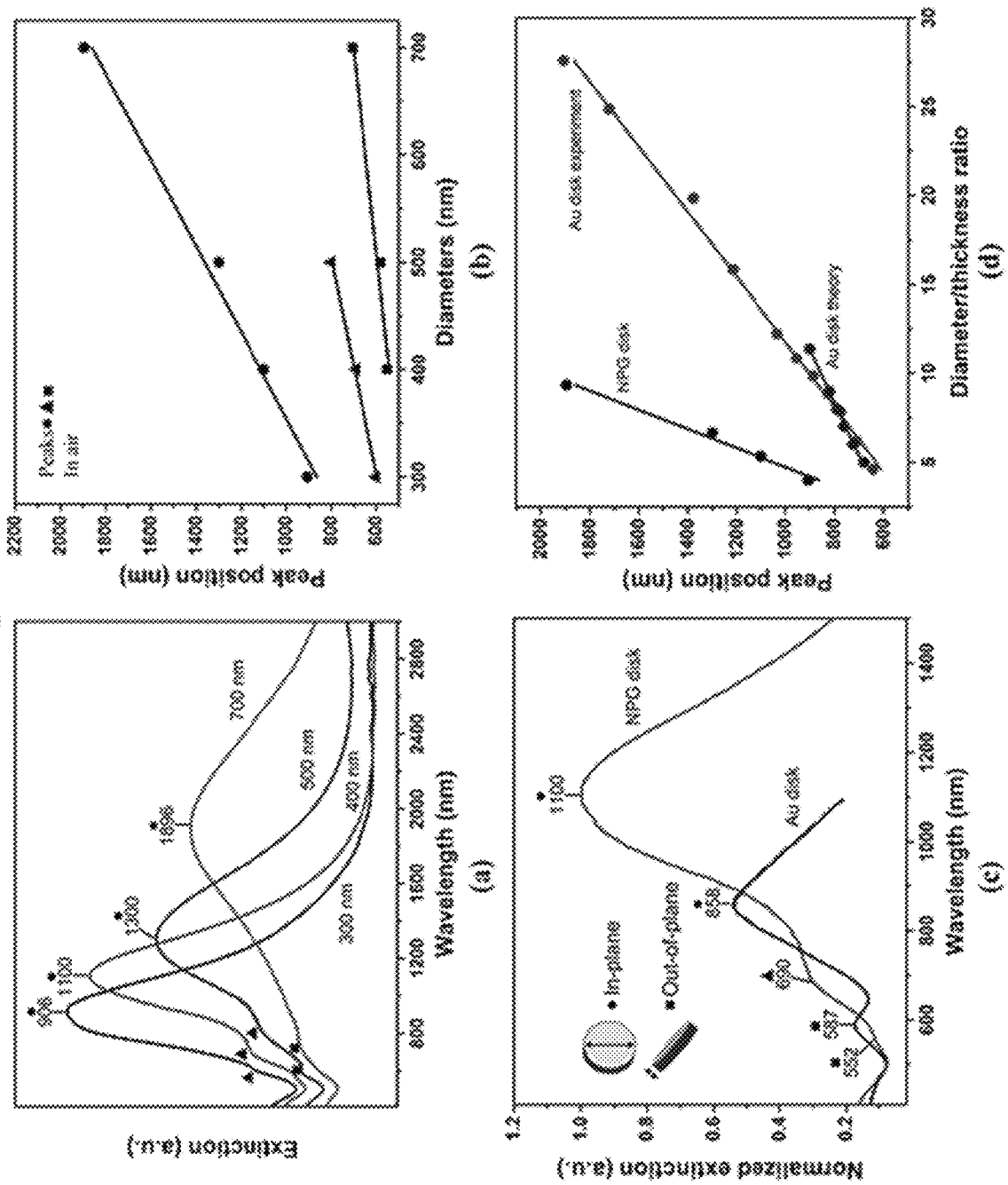
FIG. 5 shows (a) extinction spectra of NPG disks with different diameters in air, (b) plasmonic resonance peak positions versus NPG disk diameter in air, (c) extinction spectra of 400 nm diameter and 75 nm thickness Au disks and NPG disks on glass substrates measured in air, and (d) in-plane dipole resonance peak positions plotted as a function of the diameter/thickness ratio.

The plasmonic properties of NPG disks can be first understood by comparing with semi-infinite NPG thin films. FIG. 5 shows size-dependent plasmonic properties of NPG disk and comparison with Au disk. FIG. 5(a) shows extinction spectra of NPG disks with different diameters: 300, 400, 500, and 700 nm. The samples consisted of high-density NPG disk monolayers on glass substrates in air (n=1). FIG. 5(b) shows plasmonic resonance peak positions versus NPG disk diameter in air. FIG. 5(c) shows extinction spectra of 400 nm diameter and 75 nm thickness Au disks and NPG disks on glass substrates measured in air. Both spectra were normalized to buoyant mass. The inset shows the in-plane and out-of-plane resonance modes. FIG. 5(d) shows the in-plane dipole resonance peak positions plotted as a function of the diameter/thickness ratio. NPG disks, Au experimental results and Au theoretical calculations are shown, respectively. All extinction spectra were collected at 0° normal incidence.

As shown in the extinction spectra in FIG. 5(a), three peaks have been assigned as NPG LSPR ("▲"), out-of-plane resonance ("■"), and in-plane resonance ("●"). The NPG LSPR mode originated from the nanoporous structures, whereas the in-plane and out-of-plane modes were associated with the external disk shape. Size-dependent plasmonic shifts in these peaks have been observed when the disk diameter was increased from 300 to 700 nm. Among these peaks, the in-plane resonance clearly dominates and only exists in NPG disks but not in semi-infinite NPG thin films. NPG thin films were reported to exhibit two plasmonic resonance peaks near 490 and 515 nm in air. While the 490 nm peak assigned to out-of-plane resonance ("■") was nearly fixed, the peak at 515 nm assigned to NPG LSPR ("▲") exhibited limited tunability with respect to pore size and ambient refractive index. A red-shift of this peak to 540 nm in air was observed when the pore size was varied from 10 to 30 nm. In contrast, NPG disks have highly tunable plasmonic properties for all peaks as shown in FIG. 5(a), due to plasmonic coupling between the nanoporous structures and the patterned disk shape. Also according to previous reports, unpatterned NPG thin films with pore size ~13 nm should exhibit an NPG LSPR peak ("▲") between 510 and 530 nm in air. However, with 13 nm pore size, this peak shifted to ~600 nm and nearly 800 nm for NPG disks with a diameter of 300 and 500 nm, respectively (FIG. 5(b)). In addition, the out-of-plane resonance mode ("■"), though fixed in NPG thin films, became mobile and shifted from 552 nm to 706 nm as the diameter increased from 400 to 700 nm. The peak position versus NPG disk diameter in air are summarized in FIG. 5(b).

The plasmonic properties of NPG disks can be further understood by comparing with those of Au disks having the same diameter and thickness on glass substrates (FIG. 5(c)). The two Au disk absorption peaks at 858 and 587 nm are assigned to the in-plane ("●") and out-of-plane ("■") resonance modes, respectively. At normal incidence, it is noted that the out-of-plane resonance mode begins to appear when Au disk diameter size is larger than 250 nm (thickness ~20 nm). With the large diameter, Au disk and NPG disk exhibit the out-of-plane resonance mode around 500~600 nm that agrees with the previous report. For NPG disks, as mentioned previously, there are three peaks at 1100, 690 and 552 nm. The peaks at 1100 and 552 nm correspond to the in-plane ("●") and out-of-plane ("■") resonance modes due to the disk shape, respectively, while the additional peak at 690 nm originates from the NPG LSPR ("▲") generated by the nanopores and nanoscale Au ligaments. Compared to Au disks, the plasmonic bands of NPG disks exhibits a remarkable red shift (i.e., the in-plane resonance) from 858 to 1100 nm compared to Au disks. It could be interpreted by plasmonic coupling (or plasmon hybridization). As for simple metal nanoparticles, plasmonic coupling gives rise to a red shift in the plasmon as the distance between two nanoparticles decreases. However, in the case of NPG disks, the distances between disks on the substrates are random in the region from 0.1 to 1 μm, and thus the coupling effect caused by the inter-disk distances is greatly reduced. The red shift must be caused by coupling between the 3-dimensional bicontinuous porous nanostructures and the outer geometrical size and shape. Such coupling is observed as spectral overlap between the in-plane resonance and the NPG LSPR. By normalizing the extinction spectra to their respective buoyant mass measured on a single-particle basis (FIG. 5(d)), it is found that the peak height of the in-plane mode of NPG disks is about twice that of Au disks of the same external geometry. The NPG disk also shows a much broader in-plane peak compared to the Au disk: 460.9 versus 284.0 nm for the full width at half maximum (FWHM). Overall, the total extinction per buoyant mass for NPG disks is 3.3 times that of Au disks. The peak broadening can be attributed to random nanoporous structures and nanoscale Au ligaments.

Since it is known that Au disks exhibit a size-dependent shift in one or more of the plasmonic resonance peaks due to changes electromagnetic retardation, similar behavior is expected in NPG disks. As shown in FIG. 5(b), the UV-VIS-NIR extinction spectra of NPG disks of different sizes indicate that the in-plane dipole resonance mode ("●") red shifted from 906 to 1896 nm when the disk diameter was increased from 300 to 700 nm. For Au disks, previous results revealed that the red shift of the in-plane resonance mode peak was around 40 nm per diameter-to-thickness ratio (DTR) ($\lambda$/dDTR). In contrast, NPG disks exhibit a 4.5 times larger d$\lambda$/dDTR of 187 nm, suggesting larger tunability than that of Au disks by geometrical modifications. Peak positions vs. the DTR for NPG disks and Au disks are shown in FIG. 5(d). As alluded to earlier, another feature of NPG disks is the peak broadening compared to Au disks as the diameter increases from 300 to 700 nm (Table 1). Besides the in-plane resonance peak ("●"), the out-of-plane ("■") and the NPG LSPR ("▲") peaks have qualitatively similar red shifts as the diameter increases. This has never been observed in NPG-related materials as discussed previously.

Figure 6:
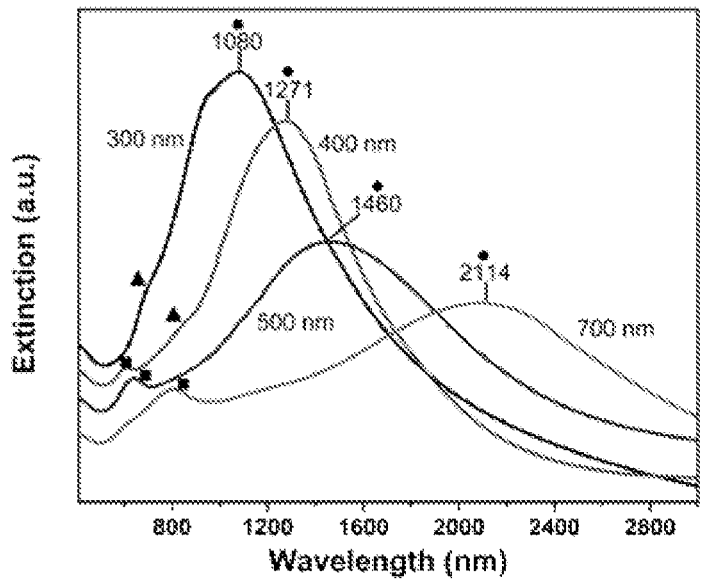
FIG. 6 shows (a) extinction spectra of NPG disks with different diameters in water, (b) extinction spectra normalized to buoyant mass of 400 nm diameter and 75 nm thickness Au disks and NPG disks on glass substrates measured in water.
Figure 6:
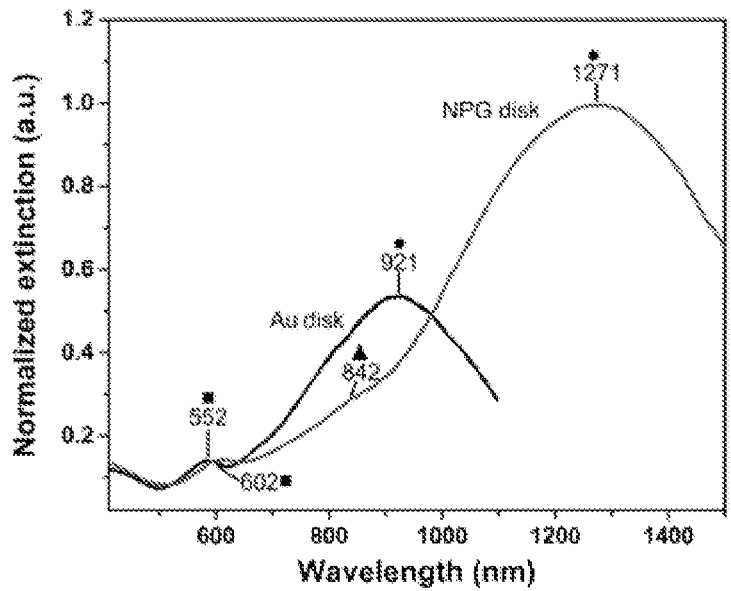

NPG disk plasmon resonance is variable due to refractive index changes in the ambient environment. It is well known that plasmon resonance is sensitive to the surrounding medium and exhibits peak shifts, which can be quantified by a sensitivity factor d$\lambda$/dn with the units of nm per refractive index unit (nm/RIU). The plasmonic properties of NPG disks and Au disks were examined in water (n=1.33). FIG. 6 shows (a) extinction spectra of NPG disks with different diameters: 300, 400, 500, and 700 nm in water (n=1.33), and (b) extinction spectra normalized to buoyant mass of 400 nm diameter and 75 nm thickness Au disks and NPG disks on glass substrates measured in water. The extinction spectra shown in FIG. 6(a) suggest the sensitivity factor d$\lambda$/dn for the NPG LSPR peak ("▲") of 400 nm NPG disks was ~456 nm, much larger than those observed for NPG thin films. Indeed, the unique nanoporous structure makes NPG disks more sensitive to the surrounding medium than either Au disks or unpatterned NPG thin films. As shown in FIG. 6(b), the peaks of the in-plane resonance modes exhibited d$\lambda$/dn of 190 and 518 nm/RIU for Au disks and NPG disks by changing the ambient environment from air to water, respectively. The out-of-plane dipole resonance mode of Au disks at 587 nm did not shift, while that of the NPG disks still red shifted, with a d$\lambda$/dn of ~152 nm/RIU.

Figure 7:
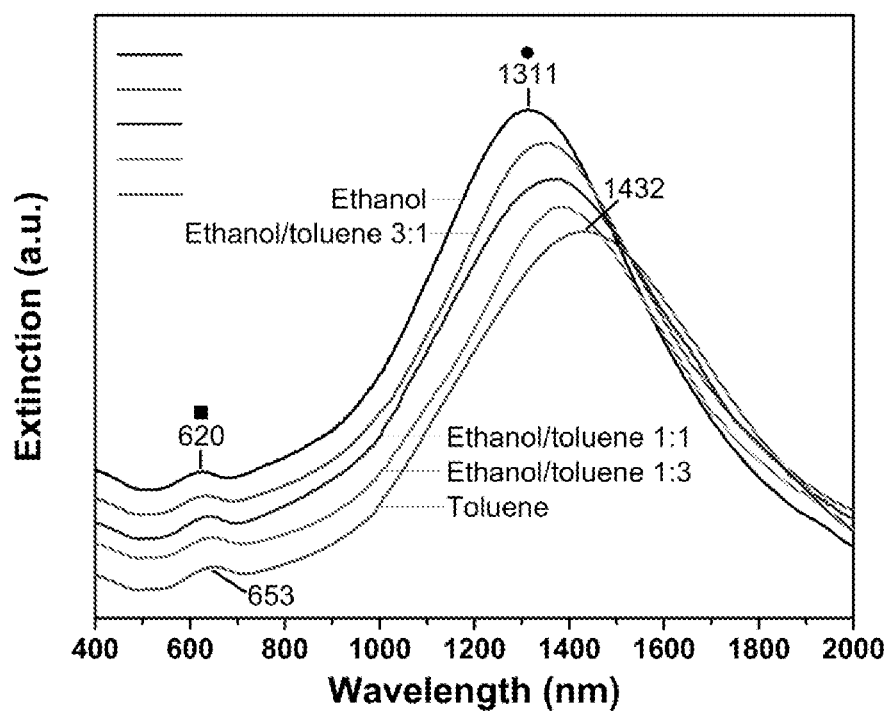
FIG. 7 shows (a) extinction spectra of 400 nm NPG disks in various solvent mixtures with known refractive indices, and (b) the peak shift of peaks marked with symbols ● and ■ plotted versus n.
Figure 7:
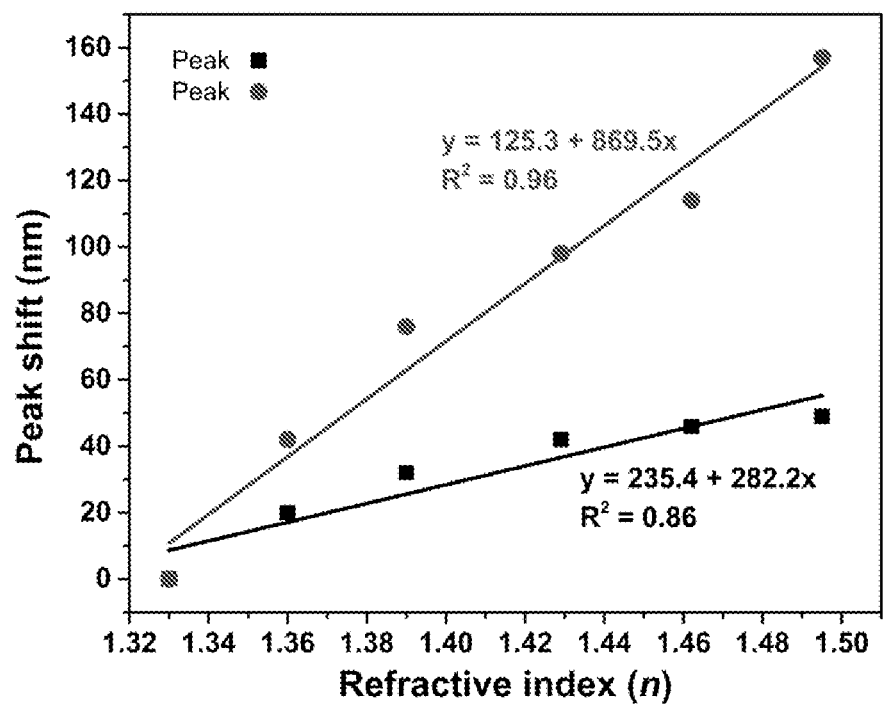

NPG disks can be used as plasmonic sensors due to the excellent sensitivity factor. To further extend the range of index sensing into those for common solvents, peak shifts of 400 nm NPG disks over the index range of 1.36 to 1.495 using pure ethanol, ethanol/toluene mixtures and pure toluene were investigated. FIG. 7 shows (a) extinction spectra of 400 nm NPG disks in various solvent mixtures with known refractive indices (n) varying from 1.36 to 1.495: ethanol (n=1.36), 3:1 ethanol/toluene (n=1.39), 1:1 ethanol/toluene (n=1.429), 1:3 ethanol/toluene (n=1.462), and toluene (n=1.495). FIG. 7(b) shows the peak shift of peaks marked with symbols ● and ■ plotted versus n. FIG. 7a illustrates the extinction spectra of the 400 nm NPG disks in these various solvents. As quantified in FIG. 7b the peaks "●" and "■" red-shifted with sensitivity factors of 869.5 and 235.4 nm/RIU, respectively. Peak shift in the NPG LSPR peak was unclear due to overlap with the broad peak "●". Overall, the sensitivity of NPG disk in-plane peak ("●") is larger than those of spherical Au nanoparticles, Ag@Au nanoshells, $SiO_2$@Au nanoshells, Au disks, Au nanorods, nanocages and silver nanoprisms, and comparable to nanorices and nanorings which range up to 800 nm/RIU.

Figure 8:
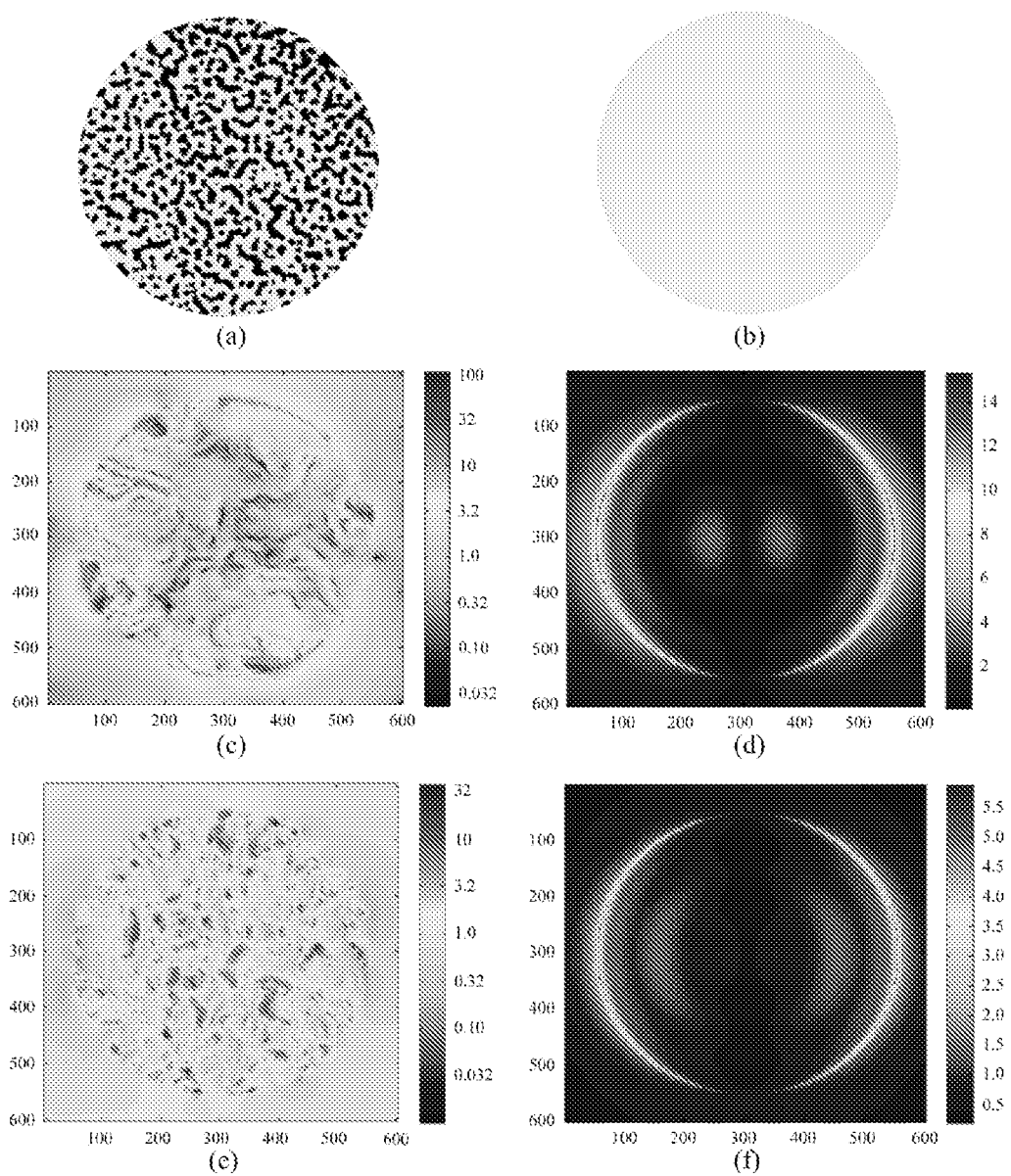
FIG. 8 shows (a) simulated E-field model for NPG disk, (b) simulated E-field model for Au disk, (c) E-field distribution of NPG disk for 1300 nm incidence wavelength, (d) E-field distribution of Au disk for 1300 nm incidence wavelength, (e) E-field distribution of NPG disk for 785 nm incidence wavelength, and (f) E-field distribution of Au disk for 785 nm incidence wavelength.

To further elucidate the observed extraordinary size- and environment-dependent plasmonic behavior of NPG disks, finite difference time domain (FDTD) simulations were performed and compared with Au disks having identical external shape parameters: 500 nm in diameter and 75 nm in thicknesses. FIG. 8 shows the E-field distribution of NPG disk and Au disk with 500 nm diameter and 75 nm thickness. FIGS. 8(a) and (b) are simulated models for NPG disk and Au disk, respectively. E-field distribution was simulated using FDTD with plane wave incidence perpendicular to the disks, horizontally polarized. FIGS. 8 (c) and (d) show E-field distribution of NPG disk and Au disk for 1300 nm incidence wavelength, respectively. FIGS. 8 (e) and (f) show E-field distribution of NPG disk and Au disk for 785 nm incidence wavelength, respectively. The NPG disk model shown in FIG. 8a was constructed directly from the SEM image shown earlier. FIG. 8c displays the calculated electric-field (E-field) distribution for 1300 nm incident wavelength, matching the in-plane resonance previously discussed. "Hot-spots" in the pores around the edges are observed with a maximum E-field enhancement factor ~100. In contrast, the Au disk in FIG. 8b produced a maximum E-field enhancement of ~15, confined to either side of the disk (FIG. 8d). Next, the E-field distribution of NPG disk for 785 nm incident wavelength was examined, matching the NPG LSPR peak previously discussed. As shown in FIG. 8e, uniformly distributed hot-spots within the entire disk are observed with a maximum E-field enhancement factor about 32. In contrast, the E-field distribution of Au disk as shown in FIG. 8f appears similar to that in FIG. 8d with a maximum enhancement factor about 6. Thus, NPG disk maintains ~6-fold higher E-field enhancement compared to Au disk.

The different patterns of hot-spot distribution in NPG disk for 1300 and 785 nm incident wavelengths are most intriguing (FIGS. 8c and e). At 1300 nm, the hot-spot distribution appears to be concentrated near the pores around edges, supporting the previous interpretation of coupling between the in-plane resonance and the pores around edges. In contrast, the uniform hot-spot distribution for 785 nm supports the interpretation that it is NPG LSPR. Of course, coupling was still present since the NPG LSPR sits on the tail of the in-plane resonance mode (See FIG. 5a). The 785 nm results also shed new light on the previous observation of excellent SERS with an enhanced factor exceeding $10^8$ by 785 nm excitation. Overall, the FDTD results provide further support that the plasmonic coupling originating from the random nanoporous structure and the disk shape plays a key role in the unique plasmonic properties of NPG disks.

Overall, shape- and size-controlled monolithic NPG disks were demonstrated as a new type of plasmonic nanoparticle in both substrate-bound and non-aggregating colloidal formats. NPG disks feature large specific surface area due to their internal nanoporous network. NPG disks also contain numerous plasmonic hot-spots throughout the internal volume, which has enabled the demonstration of the high LSPR sensitivity to ambient index changes. Putting NPG disks into the context of existing repertoire of gold nanoparticles, which permits tunability by varying parameters in design dimensions such as material composition, particle size, shape (e.g., sphere, rod, cube, triangle, and cage) and configuration (core-shell), the work strongly advocates porosity as yet another potential design dimension for plasmonic engineering. In addition to its excellent plasmonic properties, the gold material permits facile binding of a wide range of thiolated molecular and biomolecular species through the Au—S bond. The synergy of large specific surface area, high-density hot spots, and tunable plasmonics would profoundly impact applications where plasmonic nanoparticles and non-plasmonic mesoporous nanoparticles are currently employed, e.g., in in-vitro and in-vivo biosensing, molecular imaging, photothermal contrast agents, and molecular cargos.

Detection of Immobilized Probes on NPG Disks

There are multiple possible variations for signal detection using probes immobilized on NPG disks.

Figure 9:
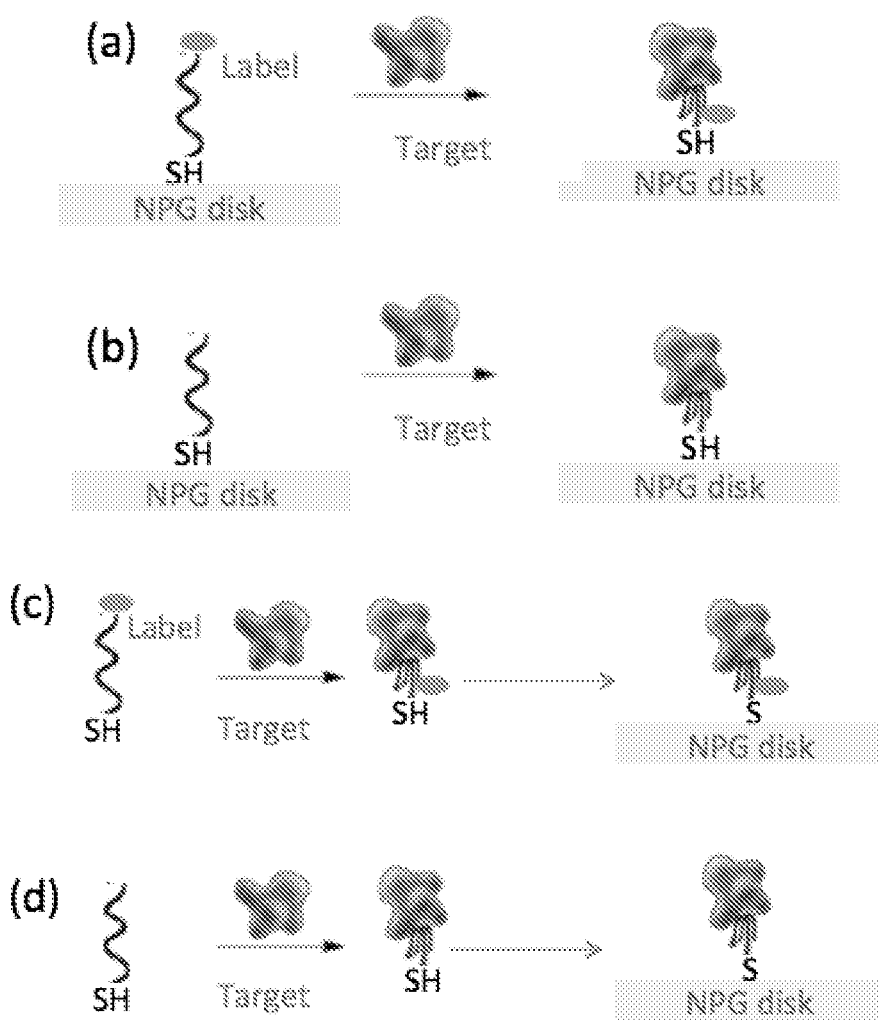
FIG. 9 shows schematics illustrating variations (a)-(d) for off-on signaling using ssDNA aptamer probes and NPG disks with or without dye.

FIG. 9 shows an example of off-on signaling with a ssDNA aptamer probe, with or without dye. In a first variation, a labeled probe molecule is immobilized on NPG disks (FIG. 9(a)) with signal detection. A target molecule is then introduced and binds with the probe with (optional) wash and signal detection during or after the binding. In a second variation, an unlabeled probe molecule is immobilized on NPG disks (FIG. 9(b)) with signal detection. A target molecule is then introduced and binds with the probe with (optional) wash and signal detection during or after the binding. In a third variation, a labeled probe molecule is mixed with a target molecule and then immobilized on NPG disks followed by (optional) wash and signal detection (FIG. 9(c)). An unlabeled probe molecule is mixed with a target molecule and then immobilized on NPG disks followed by (optional) wash and signal detection (FIG. 9(d)).

Figure 10:
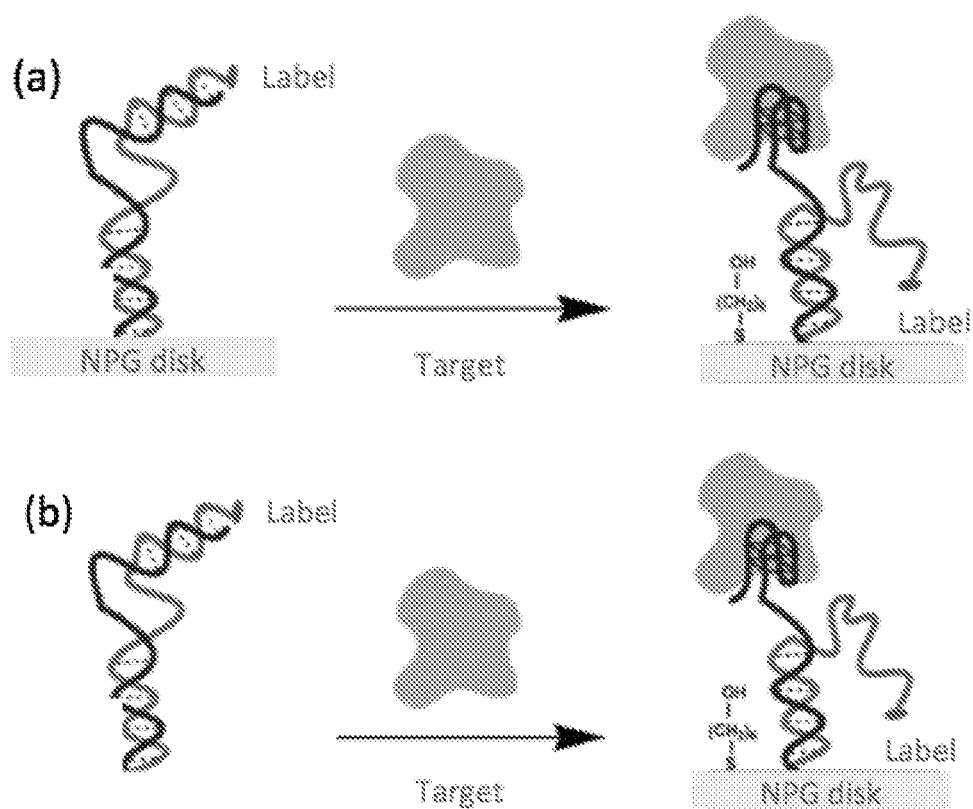
FIG. 10 shows schematics illustrating variations (a)-(b) for off-on signaling using dsDNA aptamer probes and NPG disks with dye.

FIG. 10 shows an example of off-on signaling with a dsDNA aptamer probe with dye. In a first variation, a labeled probe molecule is immobilized on NPG disks (FIG. 10(a)) with signal detection. A target molecule is then introduced and binds with the probe with (optional) wash and signal detection during or after the binding. A labeled probe molecule is mixed with a target molecule and then immobilized on NPG disks followed by (optional) wash and signal detection (FIG. 10(b)).

Figure 11:
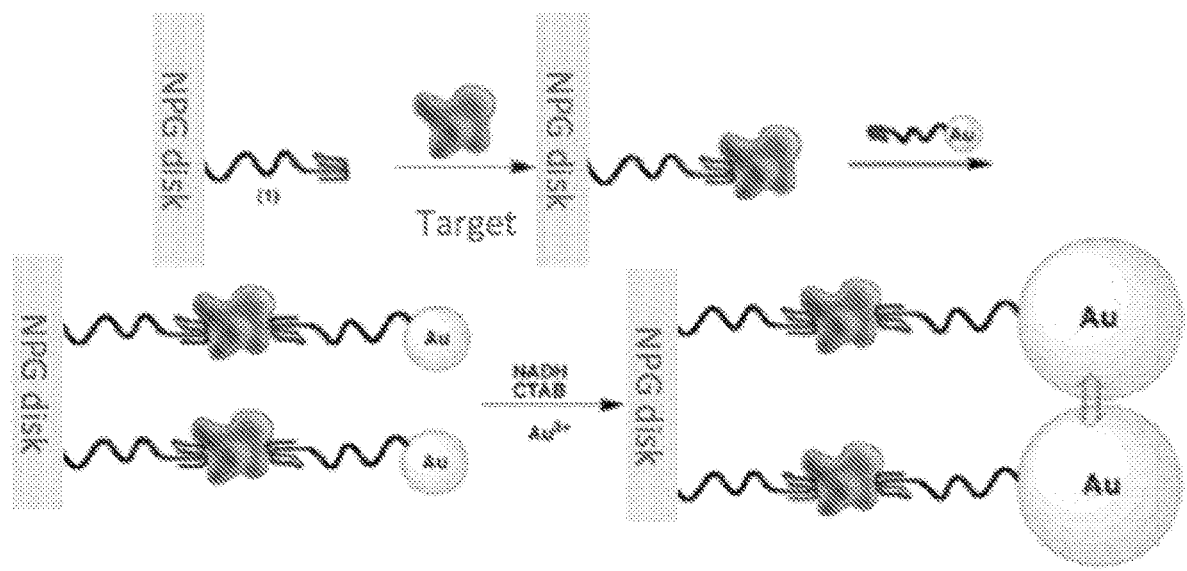
FIG. 11 shows a schematic illustrating off-on signaling using an ssDNA aptamer probe and NPG disks with Au nanoparticle or fluorescent dye signal amplifier.

FIG. 11 shows an example of off-on signaling with a ssDNA aptamer probe with Au nanoparticle or fluorescent dye signal amplifier. An unlabeled probe molecule is immobilized on NPG disks (FIG. 11) with signal detection. A target molecule is then introduced and binds with the probe with (optional) wash and signal detection during or after the binding. Another labeled probe with Au (or other materials) nanoparticles is introduced to bind the target with (optional) wash and signal detection.

Figure 12:
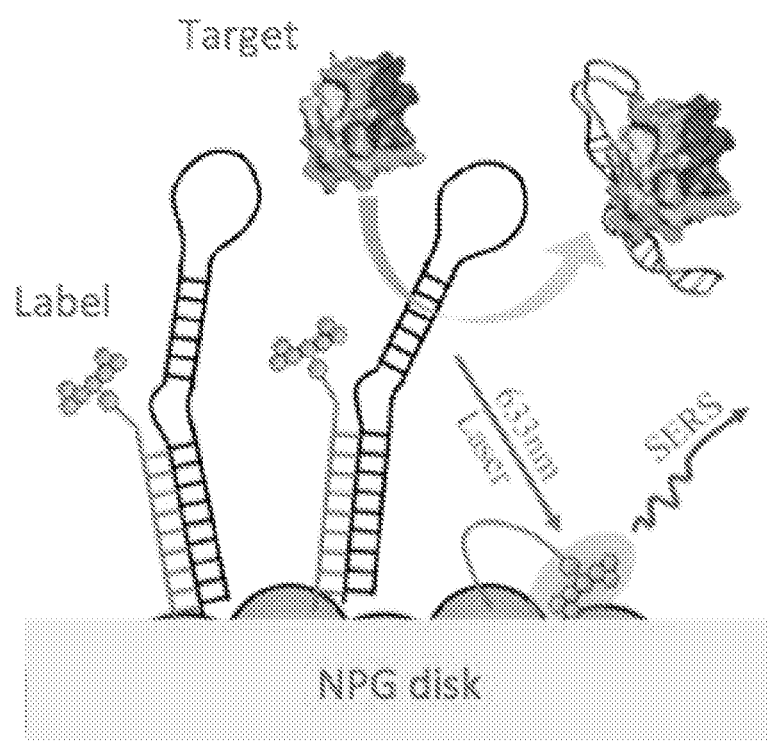
FIG. 12 shows a schematic illustrating off-on signaling using a Hoogsteen aptamer probe and NPG disk with dye.

FIG. 12 shows an example of off-on signaling with a Hoogsteen aptamer probe with dye. A labeled probe molecule is immobilized on NPG disks (FIG. 12) with signal detection. A target molecule is then introduced and binds with the probe with (optional) wash and signal detection during or after the binding.

Figure 13:
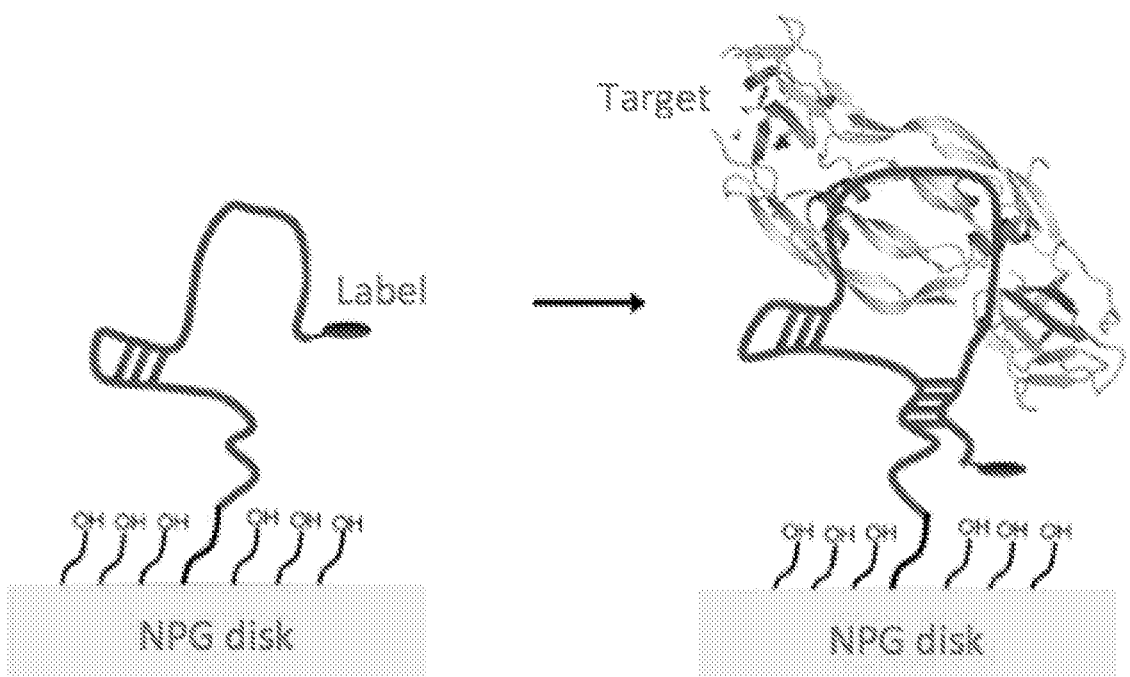
FIG. 13 shows a schematic illustrating off-on signaling using a ssDNA aptamer probe and NPG disk with dye and multiple stem-loops.

FIG. 13 shows off-on signaling using a ssDNA aptamer probe with dye and multiple stem-loops. A labeled probe molecule is immobilized on NPG disks (FIG. 13) with signal detection. A target molecule is then introduced and binds with the probe with (optional) wash and signal detection during or after the binding.

Figure 14:
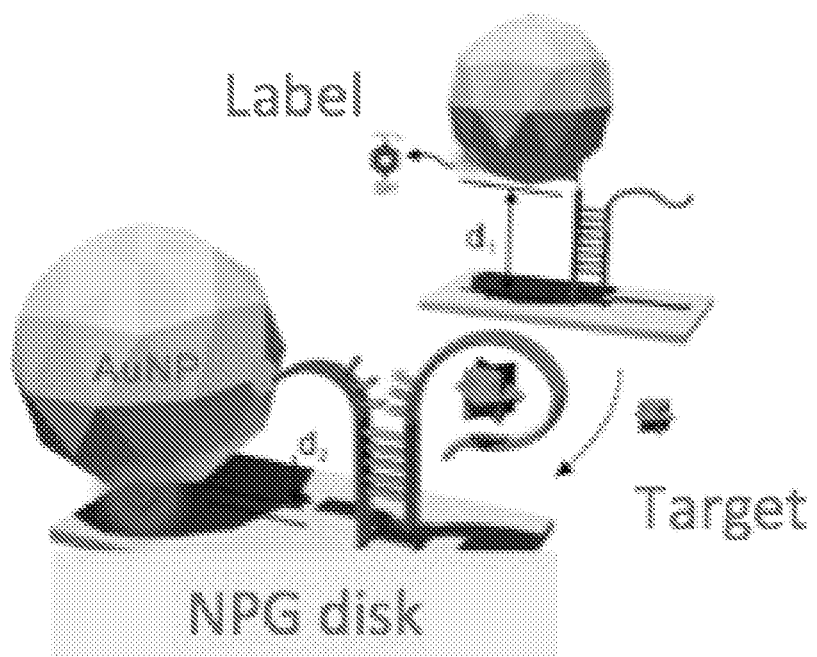
FIG. 14 shows a schematic illustrating off-on signaling using a dsDNA aptamer probe and NPG disk with dye coated Au nanoparticle.

FIG. 14 shows off-on signaling using a—dsDNA aptamer probe with dye coated Au nanoparticle. A labeled probe molecule is immobilized on NPG disks (FIG. 14) with signal detection. A target molecule is then introduced and binds with the probe with (optional) wash and signal detection during or after the binding.

Figure 15:
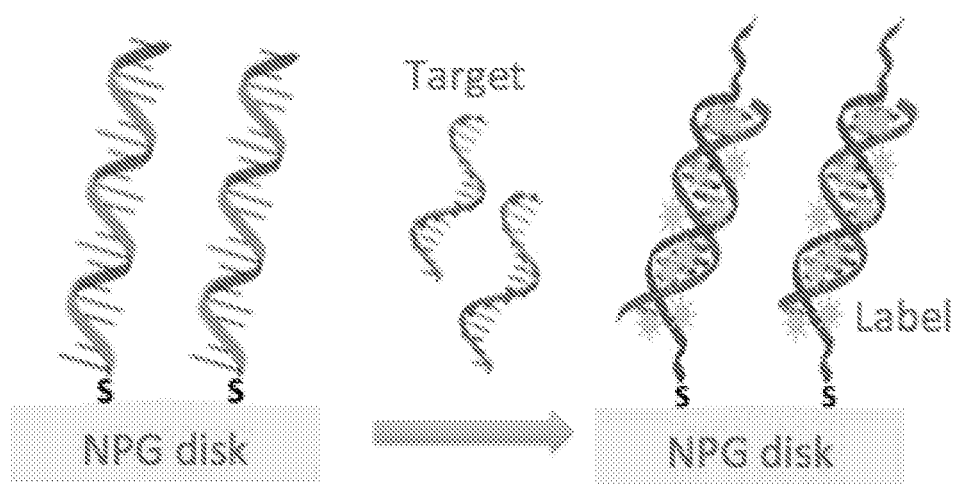
FIG. 15 shows a schematic illustrating off-on signaling using a ssDNA probe and NPG disk with molecular intercalation and trapping in major and minor grooves within dsDNA.

FIG. 15 shows off-on signaling using a ssDNA probe with molecular intercalation and trapping in major and minor grooves within dsDNA. An unlabeled probe molecule is immobilized on NPG disks (FIG. 15) with signal detection. A target molecule is then introduced and binds with the probe with (optional) wash and signal detection during or after the binding. Many label molecules are introduced to bind with (optional) wash and signal detection.

Figure 16:
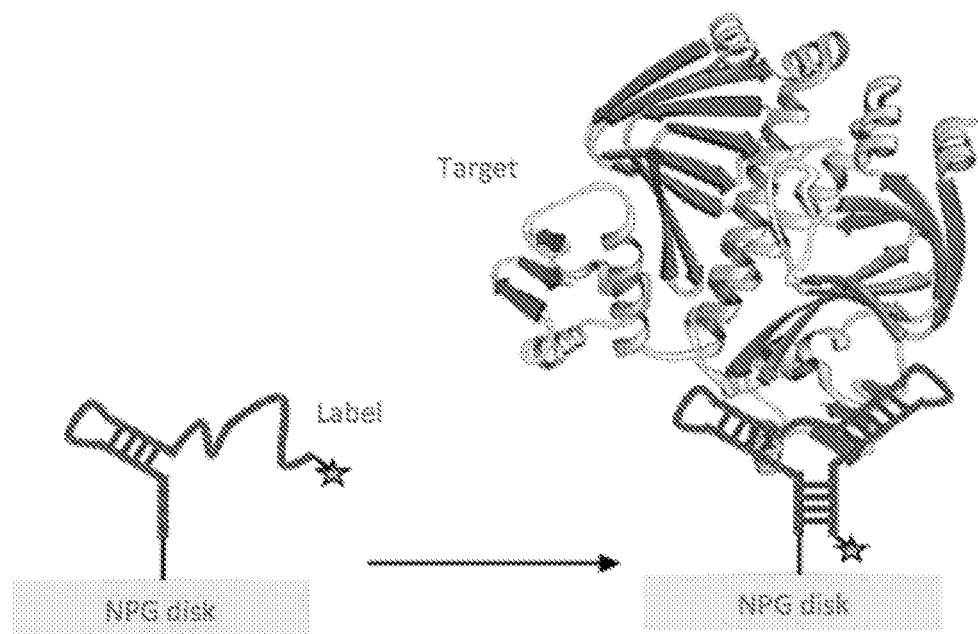
FIG. 16 shows a schematic illustrating off-on signaling using a ssDNA probe and NPG disk with multiple stem-loops and complete stem to place dye to Au surface.

FIG. 16 shows off-on signaling using a ssDNA probe with multiple stem-loops and complete stem to place dye to Au surface. A labeled probe molecule is immobilized on NPG disks (FIG. 16) with signal detection. A target molecule is then introduced and binds with the probe with (optional) wash and signal detection during or after the binding.

Example 1. Fabrication of NPG Disks

The alloy sputtering target $Ag_{825}Au_{17.5}$ (atomic percentage) was provided by ACI Alloys, INC. Argon gas (99.999%) was used for RF-sputter etching. Fusion classic syringe pumps and microliter syringes (250 µl) were purchased from Chemyx Inc. and Hamilton Company, respectively. Silicon wafers (3") were obtained from University Wafers, and the micro coverglasses (22×40 mm, No. 1) were purchased from VWR. Ethanol (200 proof) was from Decon Laboratories, Inc. Nitric acid (ACS reagent, 70%), sodium dodecyl sulfate (ACS reagent, ≥99.0%), chloroform (anhydrous, ≥99.0%), and Latex beads (polystyrene beads, 10% aqueous suspension) with mean particle sizes 0.46, 0.6, 0.8 and 1.1 µm were purchased from Sigma Aldrich.

Purchased polystyrene (PS) beads were further purified by centrifugation with a mixture of ethanol and DI water (1:1, volume ratio), and then dried in oven at 50° C. for 24 h. A 1% PS beads solution (weight ratio) was then prepared by redispersing dried PS beads in the water-ethanol solution (1:1 volume ratio). The 120-nm thick Au/Ag alloy film was deposited on the substrates such as 3" silicon wafers and the micro coverglass using an $Ag_{82.5}Au_{17.5}$ alloy target, and then the substrate was first placed into a Petri dish (3.5" in diameter) containing DI water. The as-prepared PS bead solution was slowly injected at the air/water interface with a syringe pump at a rate of 50 µL/min. The monolayer of PS beads spontaneously formed at the air/water interface. Formation of the highly patterned monolayer was further driven by the addition of 5 mM sodium dodecyl sulfate aqueous solution at the water surface. Finally, the assembled monolayer was transferred onto a substrate with the alloy film by carefully lifting it out from the air/water interface and then dried at room temperature.

The Au/Ag alloy film covered with PS the bead monolayer was first etched in oxygen plasma between 2 and 5 min to shrink the PS beads (2 min for 460 nm PS beads, 3 min for 600 and 800 nm PS beads, and 5 min for 1100 nm PS beads). The pressure and power were 30 mTorr and 100 W, respectively. After treatment with oxygen plasma, the sample was further etched in a 2 mTorr/100 W Argon plasma for 12 min to obtain Au/Ag alloy disks. The remaining polystyrene was removed by sonication in chloroform for 1 min. Finally, the NPG disks were formed by dealloying Ag in 70% nitric acid for 1 min. The sample was washed in DI water to remove the dealloying reaction products and excess nitric acid.

The NPG disks were characterized by a scanning electron microscope (PHILIPS FEI XL-30 FEG SEM). The buoyant mass of NPG disks was measured in an aqueous suspension using Archimedes particle metrology system (Affinity Biosensors, CA) to characterize further the distribution of NPG disks with single particle resolution. XPS spectra were obtained using a PHI 5700 system equipped with a monochromatic Al Kα X-ray source (hv=1486.7 eV). IR spectra were recorded with a Nicolet iS50 FT-IR spectrometer. A zeta potential analyzer from Particle Sizing Systems, Inc. (Nicomp 380 ZLS), operating in PALS mode, was used to measure the zeta potential of different aqueous NPG disk solutions at room temperature. A Cary 50 Scan UV-visible spectrometer was used to measure the UV-vis spectra ranging from 400 to 1000 nm, and the NIR region from 915 to 3000 nm was recorded with a Bruker Tensor 27 FT-NIR spectrometer.

Figure 18:
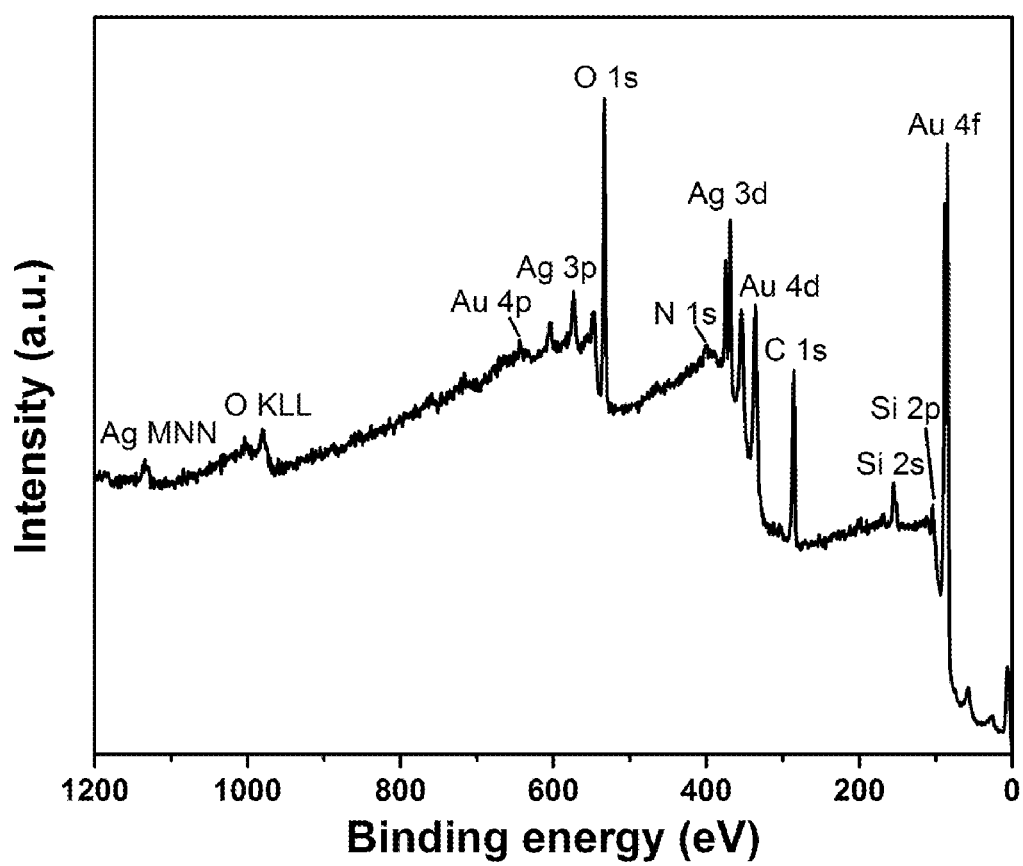
FIG. 18 shows the XPS spectrum of NPG disks.
Figure 19:
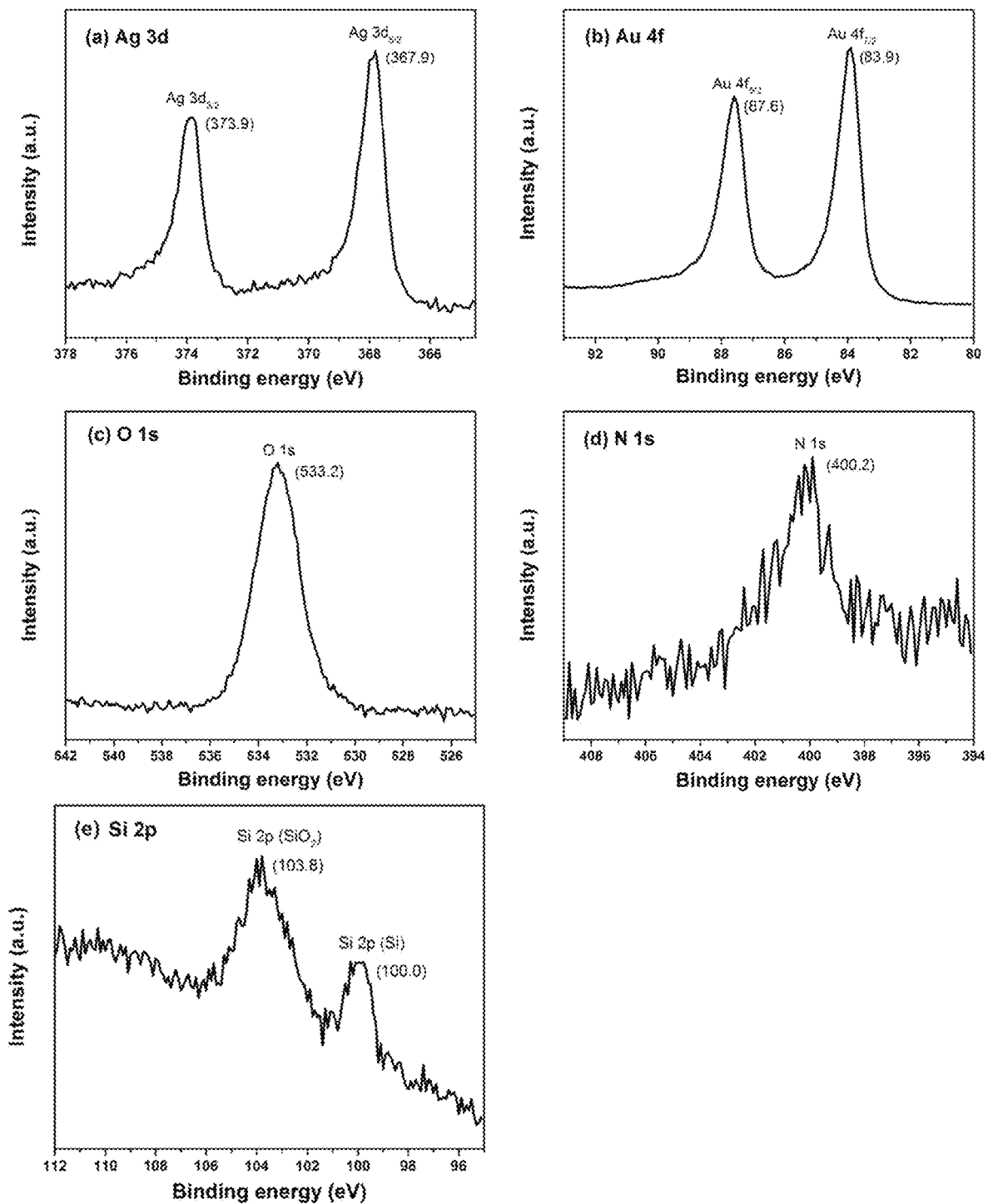
FIG. 19 shows the XPS spectra of the following regions: (a) Ag 3d, (b) Au 4f, (c) O 1s, and (e) Si 2p.

FIG. 17 shows the IR spectrum of 400 nm dried NPG disks. The aqueous NPG disk solutions were completely dried in a vacuum oven at 50° C. for 4 h before the measurement. FIG. 18 shows the XPS spectrum of the NPG disks. Aqueous NPG disk samples were drop-cast on a Si wafer and then dried in air prior to analysis by XPS. FIG. 19 shows the XPS spectra of the following regions: (a) Ag 3d, (b) Au 4f, (c) O 1s, (d) N 1s, and (e) Si 2p.

The histogram of 400 nm NPG disk buoyant mass distribution, with an average of $6.04 \times 10^{-14} \pm 7.6 \times 10^{-15}$ g, is shown in FIG. 4(*d*). A Hi-Q sensor purchased from Affinity Biosensors, CA, was calibrated using NIST standard 335 nm polystyrene particles (Bangs Labs) to obtain a sensitivity (S) of mHz/fg. The buoyant mass $m_b$ is calculated using the equation $m_b = \Delta f S$, where $\Delta f$ is the change in resonant frequency of the sensor.

The buoyant mass of Au nanodisk was calculated using the equation:

$$m_b = m_o\left(1 - \frac{\rho_f}{\rho_o}\right)$$

where $m_b$ is the buoyant mass, and $m_o$ is the dry mass of the sample. The parameters $\rho_f$ and $\rho_o$ are the densities of the sample and the fluid, respectively. The calculated buoyant mass of a single Au nanodisk was $17.2 \times 10^{-14}$ g. Thus, the mass ratio of a NPG disk to an Au nanodisk is ~0.35.

Figure 20:
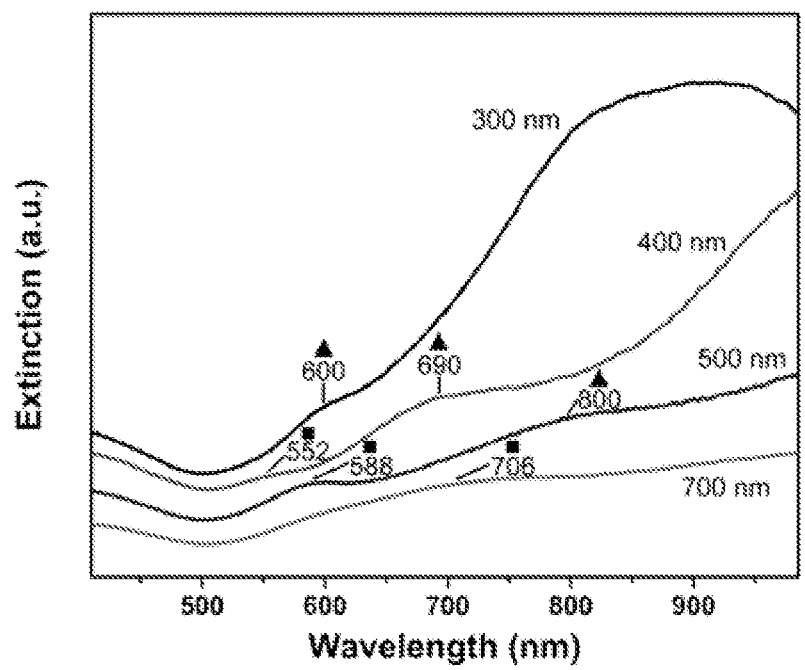
FIG. 20 shows the extinction spectra of NPG disks having different diameters over the region from 410 to 980 nm: (a) in air and (b) in water.
Figure 20:
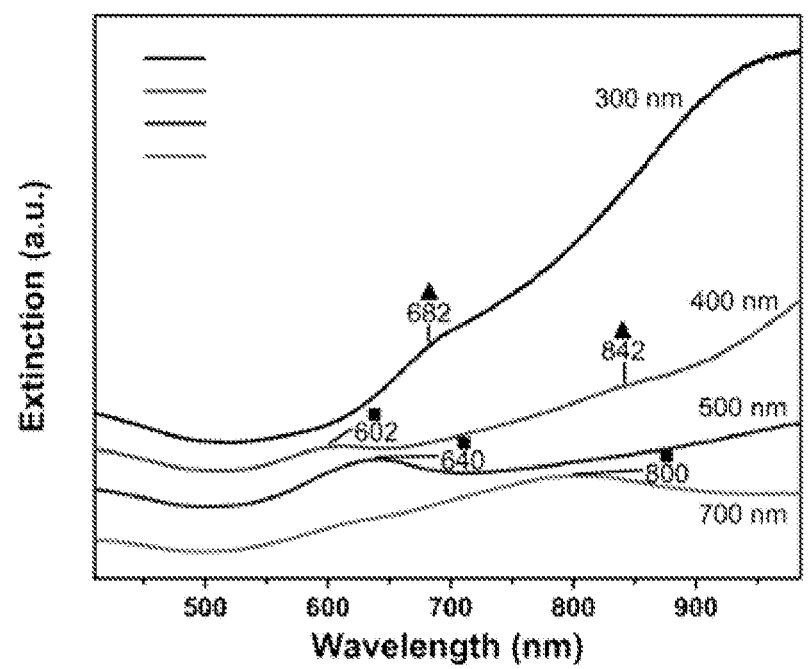

FIG. 20 shows the extinction spectra of NPG disks having different diameters over the region from 410 to 980 nm: (a) in air and (b) in water. This represents a closer view of the images shown in FIGS. 5(*a*) and 6(*a*), between 410-980 nm.

Example 2. Molecular Sentinel Probes

The ERBB2 gene (also known as ERBB2 or HER2/neu), a critical biomarker of breast cancer, was selected as the ssDNA target molecules in this example. The hairpin probe consists of a complementary sequence of ERBB2 as shown in Table 2 below ("ERBB2-sentinel"). Table 2 also shows the sequences of the ssDNA target ("ERBB-target") and non-complementary ssDNA ("Non-complementary control"). The underlined portion indicates the complementary stem sequences of the MS probe, and the bolded portion represents the target sequences complementary to the loop region of the MS hairpin probe. All ssDNA molecules were purchased from Integrated DNA Technologies (IDT, Coralville, Iowa).

TABLE 2

| Oligo-nucleotide | Sequence | SEQ ID NO. |
|---|---|---|
| ERBB2-sentinel | 5'-SH-CGCCAT CCACCCCAAGACC ACGACCAGCAGAATATGGCG-Cy3-3' | 1 |
| ERBB2-target | 5'-GTTGGCATTCTGCTGGTCGTGGTC TTGGGGGTGGTCTTTG-3' | 2 |
| Non-complementary control | 5'-GCCAGCGTCGAGTTGGTTTGCAGC TCCTGA-3' | 3 |

Monolithic hierarchical nanoporous gold disks, 500 nm in diameter, 75 nm in thickness and 5 nm in pore size, were fabricated on silicon in house. Briefly, a monolayer of 600 nm polystyrene (PS) beads was first coated onto a substrate with pre-deposited Au—Ag alloy, followed by oxygen plasma shrinkage to ensure bead separation. Argon sputter etching was then employed to transfer the pattern into the Au—Ag alloy. After the removal of the PS beads by sonication in chloroform, a 15 s dealloying was performed in concentrated nitric acid to form the NPG disks. A surface-enhanced Raman scattering enhancement factor of ~5*10$^8$ was obtained on individual disks using a benzenethiol self-assembled monolayer with 785 nm laser excitation.

MS hairpin probes were immobilized onto NPG disk substrates at the bottom of a PDMS microwell (2 mm diameter, 4 mm height) by incubation. 10 μL hairpin probe solutions were dispensed into the PDMS well and incubated for 40 min, following which the PDMS wells were removed and the substrates rinsed thoroughly in DI water. They were then immersed in 0.1 mM 6-mercapto-1-hexanol (MCH) for 10 minutes to displace the non-specifically adsorbed probe and passivate the gold surface, followed by another DI water rinse. The substrates were then mounted inside a temperature-controlled microscope microfluidic cell culture stage (FCS2, Bioptechs) with ~100 μL volume. The microscope stage was locked to ensure SERS measurements from a fixed area on the NPG disk substrates.

To better quantify and calibrate the surface density of the immobilized MS probe molecules at the low end of the tested concentration range, an alternative technique for probe immobilization was utilized by drop casting 5 μL of probe solution directly onto the NPG disk substrate. After the solution dried, the spot area (~3 mm diameter) was carefully inspected under an optical microscope and a Raman microscope to verify the coating was uniform. This allowed the estimation of the surface density of MS probes. After drop cast, the substrate was processed by the same rinse-MCH-rinse procedure described in the incubation approach.

SERS measurements were carried out using an in-house line-scan Raman microscopy system with 785 nm excitation. The laser was focused on the sample as a line with a length of 133 μm and width of 1 μm. Raman scattered photons from the entire line were imaged with 60× magnification onto the entrance slit of a dispersive spectrograph coupled to a charge coupled device (CCD) camera. The spatial and spectral resolution were ~1 μm and ~8 cm$^{-1}$, respectively. The acquisition time for each CCD frame was 10 s at a laser power density of 0.1 mW/μm$^2$. Full-frame data of dimension 133 (spatial)×1340 (λ) were collected, equivalent to 133 "point-spectra", each from a 1-μm$^2$ spot. A "line-spectrum" was obtained by averaging the 133 point-spectra in one CCD frame.

MS probes in the hairpin configuration were immobilized onto NPG disk substrates by either incubating the substrate inside a microwell filled with known concentrations of probe molecules, or drop casting 5 μL probe solution of known concentration onto the substrate, followed by rinsing with DI water. The substrate was then incubated in 0.1 mM 6-mercapto-1-hexanol (MCH) for 10 min, followed by another DI water rinse to remove non-specific molecules and passivate the gold surface. FIG. 1(b) shows SERS line-spectra from different concentrations of ERBB2-sentinel probes on NPG disk substrates by incubation (500 pM-5 nM) and drop cast (100 pM), respectively. Each line-spectrum is an average of 133 point-spectra from a single CCD frame (133 (spatial)×1340 (λ)). The baselines were approximated by a 5$^{th}$ order polynomial and removed.[37] The major peaks at 1197 cm$^{-1}$, 1393 cm$^{-1}$, 1468 cm$^{-1}$ and 1590 cm$^{-1}$ were assigned to Cy3. The presence of these major peaks indicates that the probe molecules were in their hairpin configuration, with the 3'-Cy3 near the gold surface. The Raman band at 1078 cm$^{-1}$ (marked with an asterisk) is assigned to MCH. In the following experiments, the Cy3 peak height at 1197 cm$^{-1}$ was used as the SERS intensity indicator. The immobilized probe density of drop cast onto NPG disk substrates was estimated from the number of probe molecules pipetted onto the NPG disk surface. Drop cast of 5 μL 100 pM probe solution resulted in about 2 probe molecules/μm$^2$ after previously described rinse-MCH-rinse protocol. The probe density on NPG disk substrates using the incubation method was estimated by calibrating against the SERS intensity obtained from drop cast substrates.

Example 3. Probe Density Estimation

Figure 21:
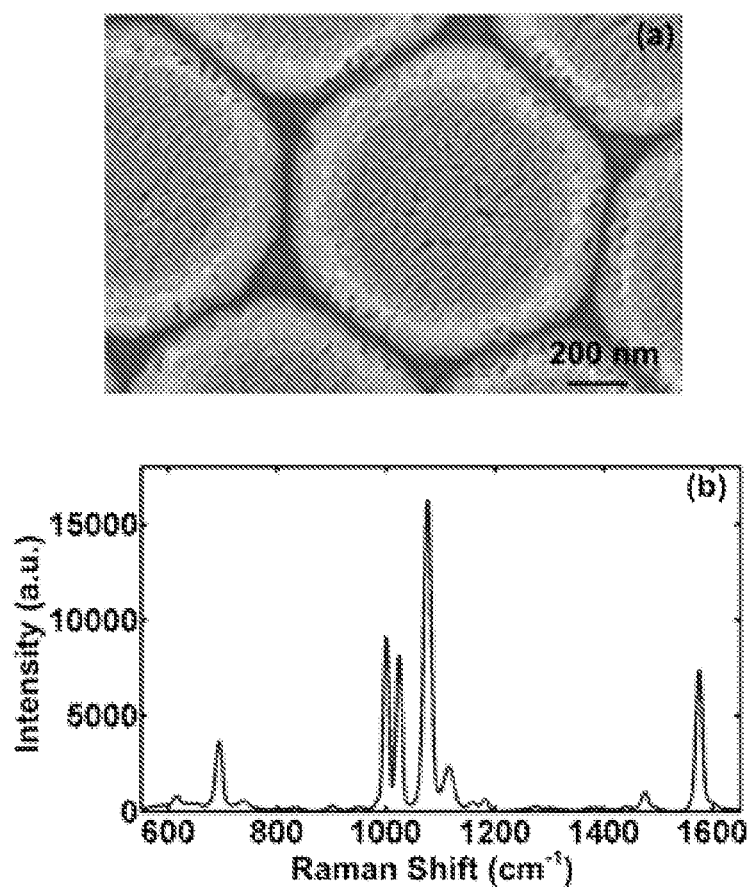
FIG. 21 shows (a) Scanning electron micrograph of NPG disks and (b) average SERS spectrum from a single NPG disk.

The NPG disks were fabricated using a combined top-down and bottom-up approach. The initial film stack, consisting of a 75 nm thick Au:Ag=28:72 alloy film over a 300 nm thick base layer of Au, was deposited by DC sputtering. The gold target was a 99.99% pure, Maple Leaf coin (Royal Canadian Mint); the alloy target was provided by ACI Alloys. The deposition rates for the gold and alloy films were 37.5 nm/min and 25 nm/min, respectively. The stack was patterned by RF-sputter-etching in 99.999% argon gas through a drop-coated mask of 500 nm polystyrene (PS) beads. RF-etching was timed to produce completely isolated alloy disks each sitting on a 65 nm thick solid gold pedestal; the remaining gold film provides a ground plane about 235 nm thick. The PS spheres were removed by sonication in isopropanol for 30 s. Ag was selectively dissolved by dipping in 70% room temperature HNO$_3$ followed by deionized water rinse and nitrogen dry to form the NPG disks. The entire dipping-transfer procedure took ~5 sec. The resulting NPG disks are shown in FIG. 21(a). Benzenethiol molecules were employed to characterize the enhancement factor (EF) since they can form self-assembled monolayer on gold surface. NPGDs was soaked in 5 nM benzenethiol solution for 30 min and rinsed in ethanol for 1 min. FIG. 21(b) shows the average SERS spectrum from a single NPG disk. The EF is calculated to be ~5×10$^8$.

Figure 22:
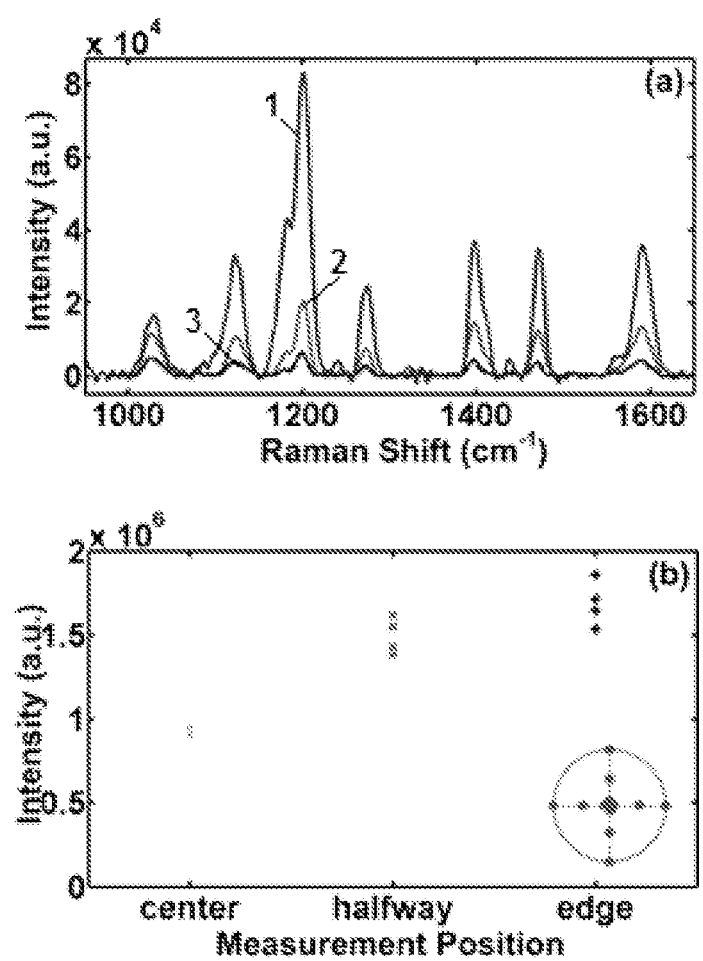
FIG. 22 shows (a) averaged SERS spectra before (1) and after (2) MCH treatment and after buffer wash step (3), and (b) Cy3 SERS intensities at different physical positions.

The average surface density of MS probe was estimated based on the measured spot area from drop cast and the volume and concentration of the MS probe solution. SERS intensity of Cy3 was used to characterize the number of probe molecules on the surface. For example, five SERS measurements were taken near the center of the dried spot by 2 µL 100 pM MS probe solution. This was to avoid taking data from the circumferences where "coffee ring" effect is apparent. The average SERS spectra are shown in FIG. 22(a). The round shaped area was ~3 mm diameter, resulting in a surface density of 42.6 molecules/µm². A~80% intensity decrease after MCH rinse was observed, suggesting the probe density was 8.5 molecules/µm². An additional 50% intensity drop was observed after the following DI water rinse, leading to 4.2 molecules. Considering the surface coverage of the NPG disks to be ~50%, the average probe density on NPG disks was about 2 molecules/µm². This represents a conservative estimate (i.e. upper bound) because the circumferences where more molecules accumulated were intentionally avoided.

The probe density distribution was also studied over the entire dried spot. Four SERS measurements were performed at the center, halfway and circumference of the dried spot, respectively. FIG. 22(b) shows the Cy3 intensities at different positions just after the final rinse. The 12 dots and the circle schematically in the lower right corner represent measurement positions with respect to the dried spot. Cy3 intensities were lower at the center and higher at the edge. This again suggests the probe density estimate likely represents an upper bound. The probe density on NPG disk substrates using the incubation method was estimated by comparing the SERS intensity with the drop cast method. As shown in FIG. 1(b), the average SERS intensity from substrates incubated in 1 nM probe solution was similar to substrates using drop cast. Thus it was concluded that the probe density was about 2 molecules/µm² for NPG disk substrates incubated in 1 nM probe solution. Similarly, the probe density for NPG disk substrates incubated in 5 nM probe solution was estimated to be about 10 molecules/µm².

Example 4. In Situ Monitoring of DNA Hybridization

Before introducing the target ssDNA molecules for hybridization, fresh phosphate buffer was flowed through the microfluidic chamber for ~1 hour, during which stable SERS signals were observed, confirming reliable probe immobilization and the stability of the technique. Hybridization was then carried out using the syringe pump to deliver target solutions of known concentration into the microfluidic chamber.

Figure 23:
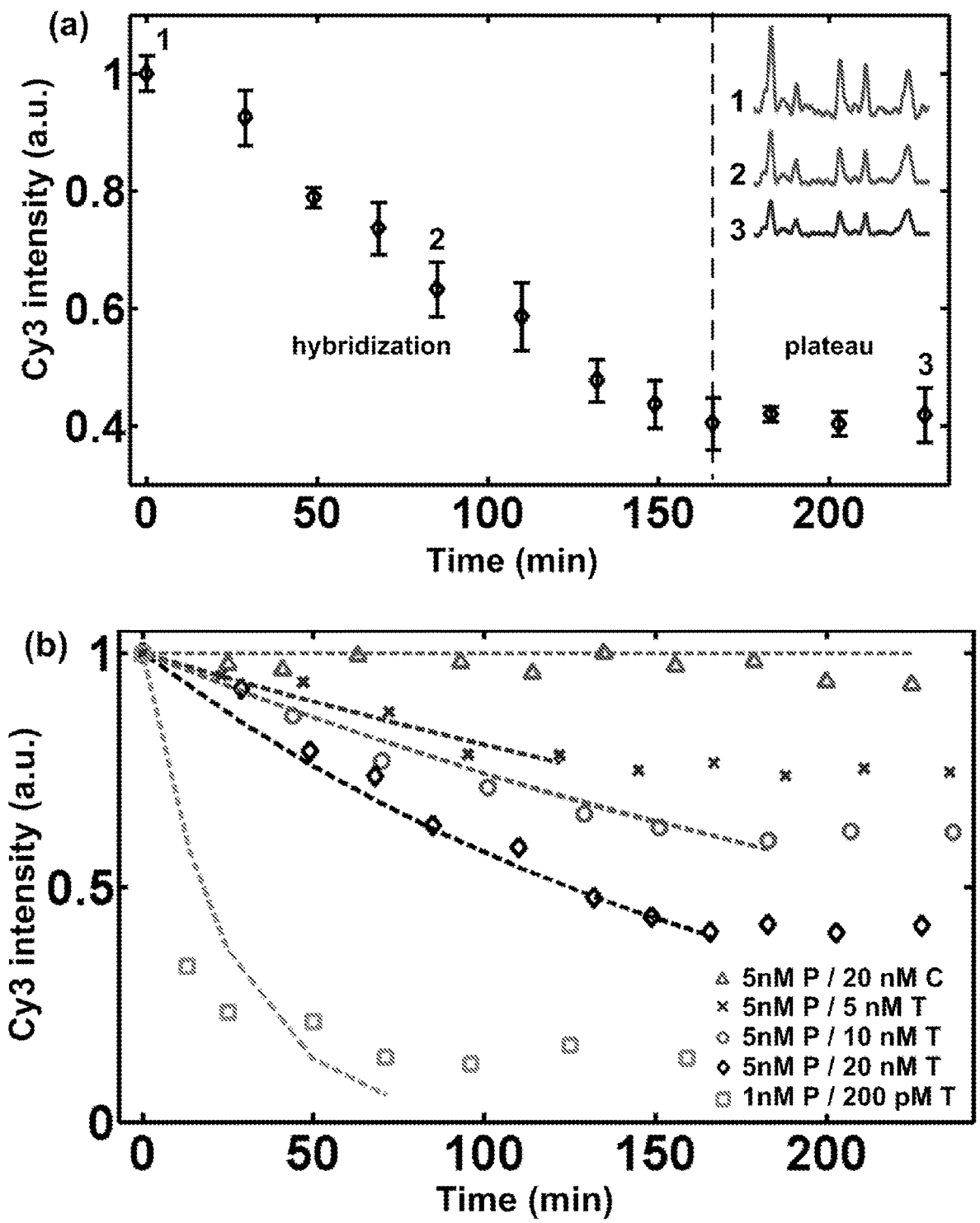
FIG. 23 shows (a) 5 nM ERBB2-sentinel probe hybridization time trace in the presence of 20 nM target DNA, (b) 5 nM ERBB2-sentinel probe hybridization time trace in the presence of 5, 10, 20 nM target (cross, circles and diamonds), 20 nM non-complementary DNA (triangles), and 1 nM ERBB2-sentinel probe hybridization time trace in the presence of 200 pM target (squares)

In the first series of experiments, the incubation technique was employed to immobilize 5 nM sentinel probe solutions, along with target concentrations from 5 to 20 nM. SERS monitoring began after the substrate was mounted into the microscope microfluidic chamber with 10-15 min acquisition intervals. For experiments using incubation at 5 nM for MS probe immobilization, a temperature of 37.5° C. was used. For the experiment using incubation at 1 nM for MS probe immobilization, 50° C. was used. FIG. 23 shows (a) 5 nM ERBB2-sentinel probe hybridization time trace in the presence of 20 nM target DNA, (b) 5 nM ERBB2-sentinel probe hybridization time trace in the presence of 5, 10, 20 nM target (cross, circles and diamonds) and 20 nM non-complementary DNA (triangles); 1 nM ERBB2-sentinel probe hybridization time trace in the presence of 200 pM target (squares). The dashed lines are the exponential fits for the curves from the hybridization phase. FIG. 23(a) shows the Cy3 intensities at 1197 cm$^{-1}$ from the line-spectra after introducing the target ssDNA molecules. Three representative line-spectra from the hybridization and the plateau phases of this experiment are shown in the upper-right corner.

As shown in FIG. 23(a), the SERS intensity began to decrease due to hybridization events after introducing the 20 nM target solution. The SERS intensity reached a plateau phase at ~170 min, indicating the completion of hybridization. Measurements over another 40 min indicated that no further hybridization occurred. A 60% SERS intensity decrease was observed from the 5 nM/20 nM (probe/target) experiment, i.e., 60% of the immobilized probes reacted with the target ssDNA molecules. A plausible explanation for the incomplete consumption of all immobilized probes is inefficient mass transfer of target ssDNA molecules to the NPG disk surface. According to the adsorption kinetics model of biomolecules, the calculation showed that only 0.003% of target ssDNA molecules were able to react with probes in the current configuration.

FIG. 23(b) shows the hybridization and plateau phase of experiments with different target concentrations and non-complementary ssDNA molecules. The dashed curves are exponential fits. A greater time constant was observed at higher target concentrations, suggesting that the target concentration can be determined by monitoring the decrease rate of Cy3 intensity. Alternatively, the final intensity value was also indicative of the target concentration. In the negative control experiment, 20 nM non-complementary ssDNA molecules did not cause a statistically meaningful SERS intensity change (±5%). Since the non-complementary ssDNA molecules could not react with the ERBB-sentinel probe, the Cy3 label remained close to the gold surface, thus maintaining a strong and stable SERS signal. Furthermore, the stable SERS signal indicated that there was no photobleaching during experiments and the probe immobilization was robust. Any signal decrease after adding target ssDNA molecules was thus attributed to hybridization. To explore the detection limit in terms of number of target DNA molecules for the sensor, the concentration of the sentinel probe was reduced to 1 nM for immobilization by incubation, resulting in a probe density of about 2 molecules/µm². The Cy3 SERS intensity time trace after adding a 200 pM target solution is displayed as squares in FIG. 23(b). The Cy3 intensity decreased significantly within the first 13 min after the introduction of target and reached a plateau phase 90 min later. About 80% overall intensity decrease was observed.

Instead of the overall time trace extracted from the line-spectra as shown in FIGS. 23(a) and (b), individual time traces from point-spectra were studied by taking advantage of the spatial resolution of the line-scan Raman system. Ideally, there were 133 time traces, each from a 1-µm² spot. Since the probe density was estimated to be about 2 molecules/µm² for substrates incubated in 1 nM MS probe solutions, and an average SERS intensities of 200 CCD counts was observed, each 100 CCD counts was interpreted as a single immobilized probe. Equivalently, each intensity decrease of 100 CCD counts during hybridization is attributed to a single hybridization event. An interval of 100 CCD counts is used between centers of bins in the following statistical analyses.

Figure 24:
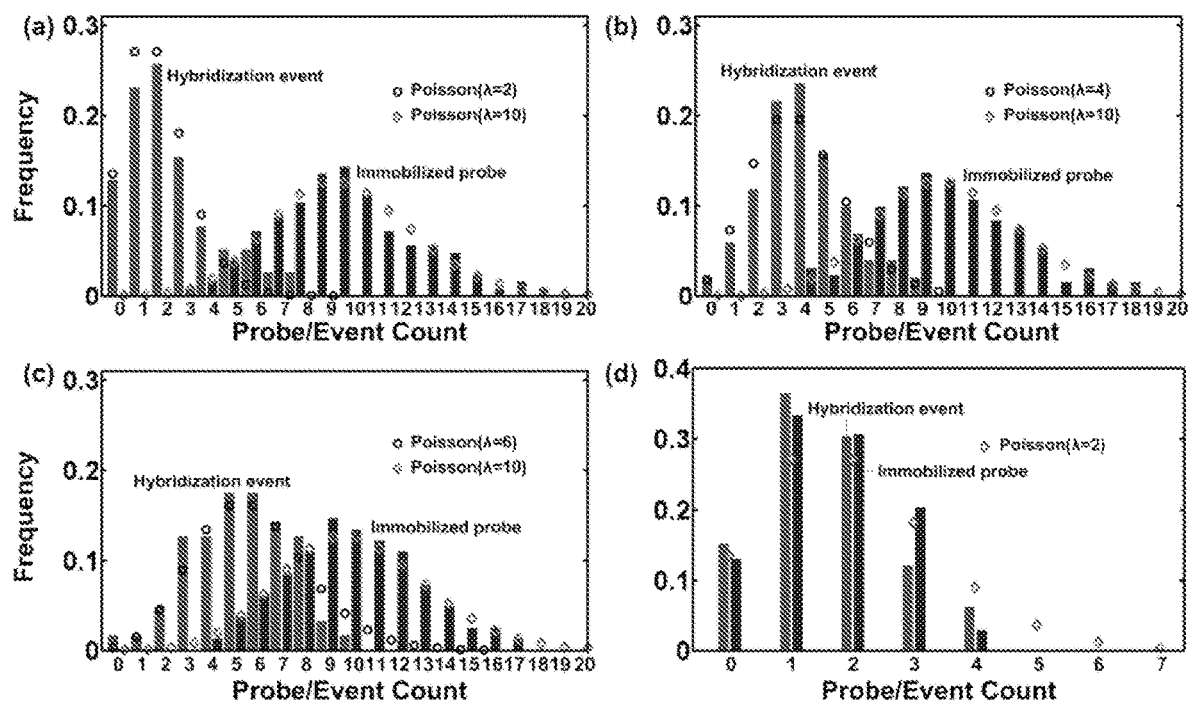
FIG. 24 shows statistical analyses of individual time traces at target concentrations of (a) 5 nM, (b) 10 nM, (c) 20 nM and (d) 200 pM at probe incubation concentrations of 5 nM, 5 nM, 5 nM and 1 nM, respectively.

FIG. 24 presents the histograms of immobilized probe counts and hybridization event counts by studying individual time traces. FIG. 24 shows statistical analyses of individual time traces at target concentrations of (a) 5 nM, (b) 10 nM, (c) 20 nM and (d) 200 pM at probe incubation concentrations of 5 nM, 5 nM, 5 nM and 1 nM, respectively. The bars centered toward the right of the histograms show the frequency of immobilized probe counts. The bars centered toward the left of the histogram represent the frequency of hybridization event counts. The total number of time traces under statistical analysis is 106, 101, 112 and 93 for target concentrations 5 nM, 10 nM, 20 nM and 200 pM, respectively. The histogram of probe counts are compared with Poisson distributions (shown as diamonds) with averages of 10 and 2 for substrates incubated with 5 nM and 1 nM probe solution, respectively. Similarly, the histogram of number of hybridization events are also compared with Poisson distribution (shown as circles in FIG. 24(a)-(c), diamonds in FIG. 24(d)) with averages of 2, 4, 6 and 2 for 5 nM, 10 nM, 20 nM and 200 pM target concentrations, respectively.

The point-spectra showing extremely high SERS intensities at different peak locations different from Cy3, likely from impurities in the solution, were excluded from the statistical study. The number of time traces involved in the statistical analyses are 106, 101, 112 and 93 for probe-to-target pairs of 5 nM/5 nM, 5 nM/10 nM, 5 nM/20 nM and 1 nM/200 pM, respectively. The bars centered toward the right of the histogram in FIG. 24 represent the frequency of the probe molecule counts immobilized on 1-μm² NPG disk surface before hybridization. Both Gaussian and Poisson distributions with least square regression were employed to fit the histograms. These histograms appear to be better fitted by Poisson distributions with an average of 10 and 2 for substrates incubated in 5 nM and 1 nM probe solutions, respectively. This agrees well with the previous interpretation that 100 CCD counts represent a single probe.

The bars centered toward the left of the histogram show the frequency of hybridization event counts. More hybridization events were observed at higher target concentrations in 5 nM incubation experiments, which is consistent with the intensity time traces in FIG. 23(b). Similarly, the histograms of hybridization event counts fit better with Poisson distributions with averages of 2, 4, 6, and 2 for 5 nM, 10 nM, 20 nM and 200 pM target solutions, respectively. In other words, 2, 4, 6, and 2 hybridization events were observed on average for 5 nM, 10 nM, 20 nM, and 200 pM target solutions, respectively.

Figure 25:
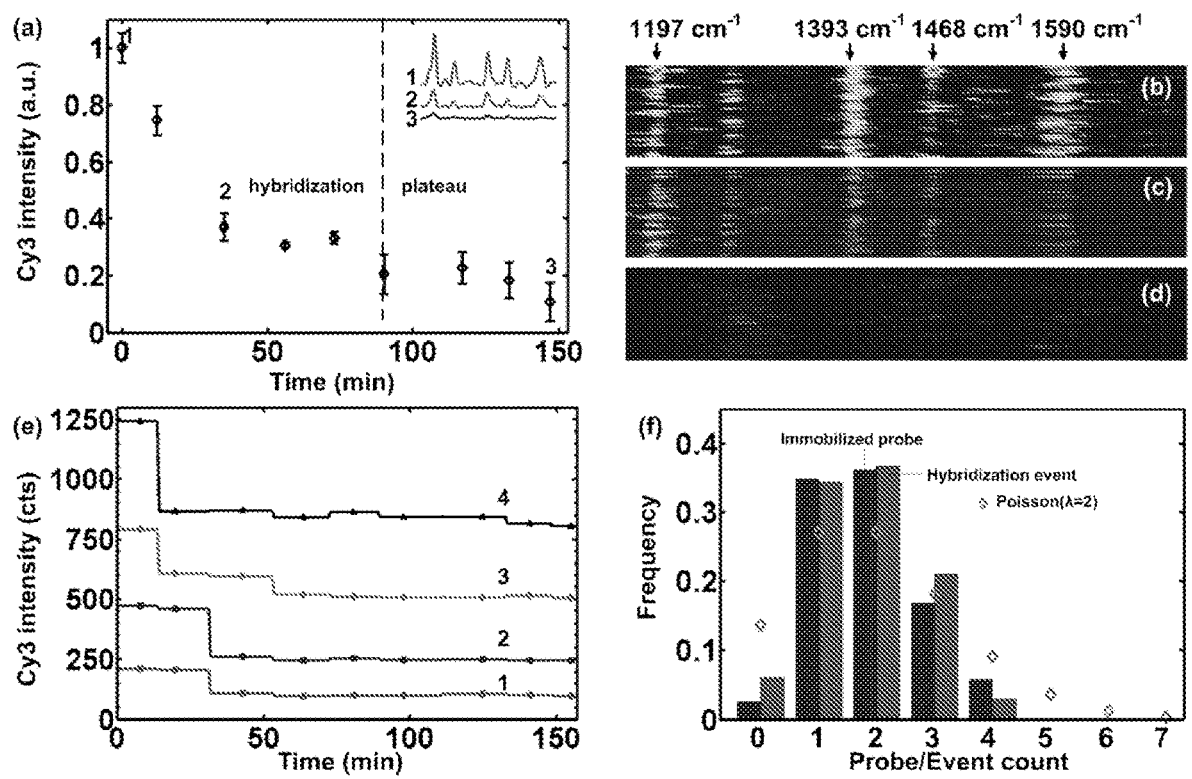
FIG. 25 shows (a) overall Cy3 intensity trace in presence of 20 pM target DNA, SERS images at (b) t=0 min, (c) t=40 min and (d) t=150 min, with the horizontal axis representing the wavenumber, (e) typical individual time traces, and (f) statistical analysis of 64 individual time traces.

In a next series of experiments, drop cast was employed as an alternative approach for probe immobilization. A temperature of 50° C. was used. The probe surface density by drop cast of 100 pM probe solutions is equivalent to that from incubating in 1 nM solutions, with both method resulting in about 2 probe molecules/μm² before hybridization. A protocol identical to the previous experiment was followed except that a 20 pM target solution was used. FIG. 25 shows (a) Overall Cy3 intensity trace in presence of 20 pM target DNA; SERS image at (b) t=0 min, (c) t=40 min and (d) t=150 min; the horizontal axis represents the wavenumber. Each row in the SERS image is a single point-spectrum. The major bands of Cy3 are labeled. FIG. 25(e) shows typical individual time traces: Trace 1, Trace 2 and Trace 4 has a stepwise intensity decrease of 100 CCD counts, 200 CCD counts and 400 CCD counts, respectively; Trace 3 has two stepwise intensity decreases, with 200 CCD counts in first decrease and 100 CCD counts in the second. FIG. 25(f) shows statistical analysis of 64 individual time traces, the bars on the left present frequency of immobilized probe counts during the probe stabilization phase, the bars on the right show the frequency of hybridization event counts. Both frequency distributions compared well with a Poisson distribution with λ=2.

As shown in FIG. 25(a), the line-spectra SERS intensity decreased substantially after the 20 pM target was introduced. Hybridization events were detected as early as 10 min after adding the target ssDNA molecules. FIGS. 25(b), (c) and (d) show the full-frame SERS images just before adding the target, during hybridization and at the last measurements (time points 1, 2 and 3 in FIG. 25(a)), respectively. The major peaks from Cy3 clearly visible in FIG. 25(b) all disappeared in FIG. 25(d). Finally, it was observed that Cy3 intensity decreased by ~80% by 90 min after introducing the target. As shown in FIG. 25(f), the histograms of the immobilized probe counts agree well with Poisson distribution with average equal to 2. A similar distribution is observed in the histogram of hybridization event counts as discussed later. Analyzing the point-spectra from 64 spots, four representative intensity patterns are observed and shown in FIG. 25(e). Trace 1, Trace 2 and Trace 4 exhibit a single-step intensity drop of 100 CCD counts, 200 CCD counts and 400 CCD counts, respectively. Trace 3 exhibits a two-step intensity drop with 200 CCD counts in the first step and then 100 CCD counts in the second. The observation of quantized intensity decreases in individual time traces provide further evidence that individual hybridization events were observed. In the experiment using incubation in 1 nM probe solution, similar quantized intensity decreases in individual time traces were also observed. The intensity patterns 1-4 correspond to 1-4 hybridization events taking place on the 1-μm² spots.

Using the representative intensity patterns shown in FIG. 25(e), statistical analysis of 64 individual hybridization time traces were performed with results shown in FIG. 25(f). As mentioned earlier, the bars on the left represent the statistics of immobilized MS probes. The bars on the right represent total hybridization events during the hybridization phase over individual 1-μm² spots. Both histograms can be better fitted with a Poisson distribution of λ=2 (diamonds in FIG. 25(f)) than with Gaussian distribution. Although there has been debate on whether to expect a Poisson distribution of SERS intensities at ultra-low concentrations, here it is only employed to provide additional insight for the results, not to justify the claim of single-molecule detection. In addition, the enhancements of SERS signals of the NPG disk substrates were uniform across a large area (at least 100×100 μm²). Therefore, measurements of SERS intensities are reliable, and not affected by factors that could potentially invalidate interpreting Poisson statistics as single-molecule events.

Within the context of microfluidic sensors, the static or laminar flow nature poses significant challenges for achieving low LOD. Unlike sensors implemented in un-restricted fluidic environments, e.g., beaker, where active mixing is readily available, the transport of target molecules to the sensing surface largely depends on diffusion in microchannels. Compared with several recently published label-free microfluidic sensors, the demonstrated LOD (20 pM) is respectable even without any attempt of optimization. After all, the technique does have single-molecule sensitivity. Also, it is quite possible to lower the LOD with the help of active concentrating mechanisms such as dielectrophoresis.

Example 5. Detection of Pathogens

NPG disks functionalized with dithiobis succinimide propionate molecules coupled to antibodies to a specific pathogen and bearing adsorbed 3,3'-Diethylthiatricarbocyanine iodide are suspended into solution containing an opacifying substance which absorbs visible wavelengths of light. A set of buoyant silica microbubbles with secondary antibodies to this pathogen is placed into the solution and binds to the cubes when the agent is present. The microbubbles are floated up to the top of the solution to an observation point and appear bright if they have an NPG disk bound to them by said pathogen.

Example 6. Detection of Mirna

A human blood sample is subjected to nucleic acid isolation by phenol/chloroform extraction and silica adsorption. The isolated nucleic acids are mixed with a suspension of 200 nm NPG disks decorated with DNA probe oligonucleotides specific to a particular microRNA, and a Raman-active dye, and then a suspension of 20 nm gold particles bearing an antibody specific to RNA/DNA hybrids is added. Single-particle tracking by Raman imaging is used to measure the scattering brightness and mobility of 10,000 disks. The presence and number of a lower-mobility, higher-brightness population of particles at higher fractional concentration than seen in a control sample containing only the two types of particles is used to infer the presence and concentration of the miRNA.

Example 7. Detection of Protease Activity

A tumor biopsy specimen is macerated and centrifuged, and the extract placed in a 96-well of a microtiter plate coated with a composite of collagen and NPG disks with a lower magnetic layer and bearing a fluor whose brightness is enhanced by the NPG surface. After 30 min incubation at 37 C with gentle agitation, the plate is placed on a magnetic stand and the wells washed. The magnet is then removed, any free NPG disks are suspended by addition of buffer to each well, the liquid phase is transferred to another plate, and the NPG disks pulled down by a plate magnet and counted by fluorescence imaging. The number of particles found in a well corresponding to a given specimen is used to infer the protease activity of that specimen.

Example 8. Magnetic Force Discrimination

In this approach, the magnetic properties of the NPGD bearing magnetic elements can be used to discriminate against non-specifically bound disks prior to detection by fluorescence or Raman (intensity or imaging).

What is claimed is:

1. A device for sensing or detection of biological components or processes, comprising:
   a plurality of nanoporous metal-containing particles bound to a substrate or in colloidal suspension, wherein the nanoporous metal-containing particles are nanoporous gold disks, wherein the nanoporous gold disks are free of cracks, wherein each nanoporous gold disk has an external disk shape, wherein each nanoporous gold disk has a thickness less than 100 nm, a diameter of 300 to 700 nm, and a plasmonic resonance of 900 to 1850 nm that can be tuned by changing the diameter of the nanoporous gold disk, and wherein the nanoporous gold disks comprise a 3-dimensional interior porous network having an average pore size of about 13 nm; and
   one or more probes immobilized to the nanoporous metal-containing particles, wherein the one or more probes are capable of capturing one or more components of interest, wherein the one or more probes are immobilized externally and in the 3-dimensional interior porous network of the nanoporous gold disks, and wherein the one or more probes produce detectable signals indicative of capture of the components of interest.

2. The device of claim 1, wherein the detectable signals are detectable using surface-enhanced Raman spectroscopy (SERS).

3. The device of claim 1, wherein the one or more probes are molecular sentinel probes, wherein the molecular sentinel probes are comprised of a probe sequence of DNA formed into a stem-loop hairpin structure, wherein the components of interest comprise target ssDNA molecules, and wherein at least a portion of the probe sequence is complementary to at least a portion of a sequence of the target ssDNA molecules.

4. The device of claim 1, wherein the one or more probes are ssDNA aptamer probes, dsDNA aptamer probes, Hoogsteen aptamer probes, ssDNA probes, or a combination thereof.

5. The device of claim 1, wherein the detectable signals are detectable using surface-enhanced fluorescence (SEF), localized surface plasmonc resonance (LSPR), or surface-enhanced near infrared spectroscopy (SENIRS).

6. A device for sensing or detection of biological components or processes, comprising:
a plurality of nanoporous metal-containing particles bound to a substrate or in colloidal suspension, wherein the nanoporous metal-containing particles are nanoporous gold disks, wherein the nanoporous gold disks are free of cracks, wherein each nanoporous gold disk has an external disk shape, wherein each nanoporous gold disk has a thickness less than 100 nm, a diameter of 300 to 700 nm, and a plasmonic resonance of 900 to 1850 nm that can be tuned by changing the diameter of the nanoporous gold disk, and wherein the nanoporous gold disks comprise a 3-dimensional interior porous network having an average pore size of about 13 nm; and
one or more recognition elements immobilized to the nanoporous metal-containing particles, wherein the one or more recognition elements are capable of capturing one or more components of interest, wherein the one or more recognition elements are immobilized externally and in the 3-dimensional interior porous network of the nanoporous gold disks, and wherein the one or more recognition elements produce detectable signals indicative of capture of the components of interest.

7. The device of claim 6, wherein the one or more recognition elements are antibodies, carbohydrates, ligands, chelators, receptors, proteins, or combinations thereof.

8. The device of claim 6, wherein the detectable signals are detectable using surface-enhanced Raman spectroscopy (SERS), surface-enhanced fluorescence (SEF), localized surface plasmonc resonance (LSPR), or surface-enhanced near infrared spectroscopy (SENIRS).

9. A method for sensing or detection of biological components or processes, comprising:
exposing the device of claim 1 to a sample containing one or more of the components of interest; and
detecting signals indicative of capture of the components of interest by the device.

10. A method for sensing or detection of biological components or processes, comprising:
exposing the device of claim 6 to a sample containing one or more of the components of interest; and
detecting signals indicative of capture of the components of interest by the device.

* * * * *

UNITED STATES PATENT AND TRADEMARK OFFICE
CERTIFICATE OF CORRECTION

PATENT NO. : 10,961,564 B2  
APPLICATION NO. : 15/314219  
DATED : March 30, 2021  
INVENTOR(S) : Wei-Chuan Shih et al.

Page 1 of 1

It is certified that error appears in the above-identified patent and that said Letters Patent is hereby corrected as shown below:

In the Specification

1. In Column 5, Line 53, delete "(c) O 1s, and (e) Si 2p;" and insert -- (c) O 1s, (d) N 1s, and (e) Si 2p; --, therefor.
2. In Column 12, Line 32, delete "N is at" and insert -- N 1s at --, therefor.
3. In Column 15, Line 5, delete "FIG. 7b" and insert -- FIG. 7b, --, therefor.
4. In Column 17, Line 25, delete "Ag825Au17.5" and insert -- Ag82.5Au17.5 --, therefor.

In the Claims

5. In Column 27, Line 22, in Claim 5, delete "plasmonc" and insert -- plasmon --, therefor.
6. In Column 28, Line 20, in Claim 8, delete "plasmonc" and insert -- plasmon --, therefor.

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 3

<210> SEQ ID NO 1
<211> LENGTH: 40
<212> TYPE: DNA
<213> ORGANISM: Artificial Sequence
<220> FEATURE:
<223> OTHER INFORMATION: Hairpin probe ERBB2-sentinel

<400> SEQUENCE: 1
cgccatccac ccccaagacc acgaccagca gaatatggcg        40

<210> SEQ ID NO 2
<211> LENGTH: 40
<212> TYPE: DNA
<213> ORGANISM: Homo sapiens

<400> SEQUENCE: 2
gttggcattc tgctggtcgt ggtcttgggg gtggtctttg        40

<210> SEQ ID NO 3
<211> LENGTH: 30
<212> TYPE: DNA
<213> ORGANISM: Artificial Sequence
<220> FEATURE:
<223> OTHER INFORMATION: Non-complementary control for ERBB2-sentinel
      hairpin probe

<400> SEQUENCE: 3
gccagcgtcg agttggtttg cagctcctga        30